(12) United States Patent
David et al.

(10) Patent No.: US 6,719,840 B2
(45) Date of Patent: Apr. 13, 2004

(54) IN SITU CRYSTAL GROWTH AND CRYSTALLIZATION

(75) Inventors: Peter R. David, Palo Alto, CA (US); Nathaniel E. David, San Diego, CA (US)

(73) Assignee: Syrrx, Inc., San Diego, CA (US)

( * ) Notice: Subject to any disclaimer, the term of this patent is extended or adjusted under 35 U.S.C. 154(b) by 0 days.

(21) Appl. No.: 09/877,405

(22) Filed: Jun. 8, 2001

(65) Prior Publication Data

US 2002/0189529 A1 Dec. 19, 2002

(51) Int. Cl.[7] .................................................. C30B 7/02
(52) U.S. Cl. ......................... 117/68; 117/69; 117/200; 117/206; 117/900; 422/245.1
(58) Field of Search ................... 117/200, 206, 117/900, 68, 70; 422/245.1

(56) References Cited

U.S. PATENT DOCUMENTS

| | | | | |
|---|---|---|---|---|
| 4,908,112 A | * | 3/1990 | Pace | 204/299 R |
| 5,132,012 A | * | 7/1992 | Miura et al. | 210/198.2 |
| 5,180,480 A | * | 1/1993 | Manz | 204/302 |
| 5,296,114 A | * | 3/1994 | Manz | 204/180.1 |
| 5,485,270 A | * | 1/1996 | Freud et al. | 356/336 |
| 5,833,860 A | | 11/1998 | Kopaciewicz et al. | |
| 6,220,075 B1 | | 4/2001 | Papen et al. | |
| 6,267,935 B1 | * | 7/2001 | Hol et al. | 422/245.1 |
| 6,409,832 B2 | * | 6/2002 | Weigl et al. | 117/200 |
| 6,527,432 B2 | | 3/2003 | Kellogg et al. | |
| 2002/0029814 A1 | | 3/2002 | Unger et al. | |
| 2002/0061687 A1 | | 5/2002 | Hansen et al. | |
| 2002/0137218 A1 | | 9/2002 | Mian et al. | |
| 2002/0144738 A1 | | 10/2002 | Unger et al. | |
| 2002/0145231 A1 | | 10/2002 | Quake et al. | |
| 2002/0195046 A1 | | 12/2002 | David | |
| 2002/0195048 A1 | | 12/2002 | David | |
| 2002/0195050 A1 | | 12/2002 | David | |
| 2003/0005877 A1 | | 1/2003 | David | |

FOREIGN PATENT DOCUMENTS

WO    WO 93/06479    *    1/1993

OTHER PUBLICATIONS

Wilson et al., "Control of solvent evaporation in hen egg white lysozyme crystallization", Journal of Crystal of Growth vol. 116 1992, pp. 414–420.*

Sanjoh et al., "Spatiotemporal protein crystal growth studies using microfluidic silicon devices", Journal of Crystal Growth vol. 196 (1999) pp. 691–702.

US 2001/0011071 A1, Aug. 2, 2001, Knudsen et al., entitled "Derivatives of GLP–1 Analogs", 132 pages.

* cited by examiner

Primary Examiner—Robert Kunemund
(74) Attorney, Agent, or Firm—David J. Weitz

(57) ABSTRACT

A method is provided for determining crystallization conditions for a material, the method comprising: taking a plurality of different crystallization samples in an enclosed microvolume, the plurality of crystallization samples comprising a material to be crystallized and crystallization conditions which vary among the plurality of crystallization samples; allowing crystals of the material to form in plurality of crystallization samples; and identifying which of the plurality of crystallization samples form crystals.

38 Claims, 22 Drawing Sheets

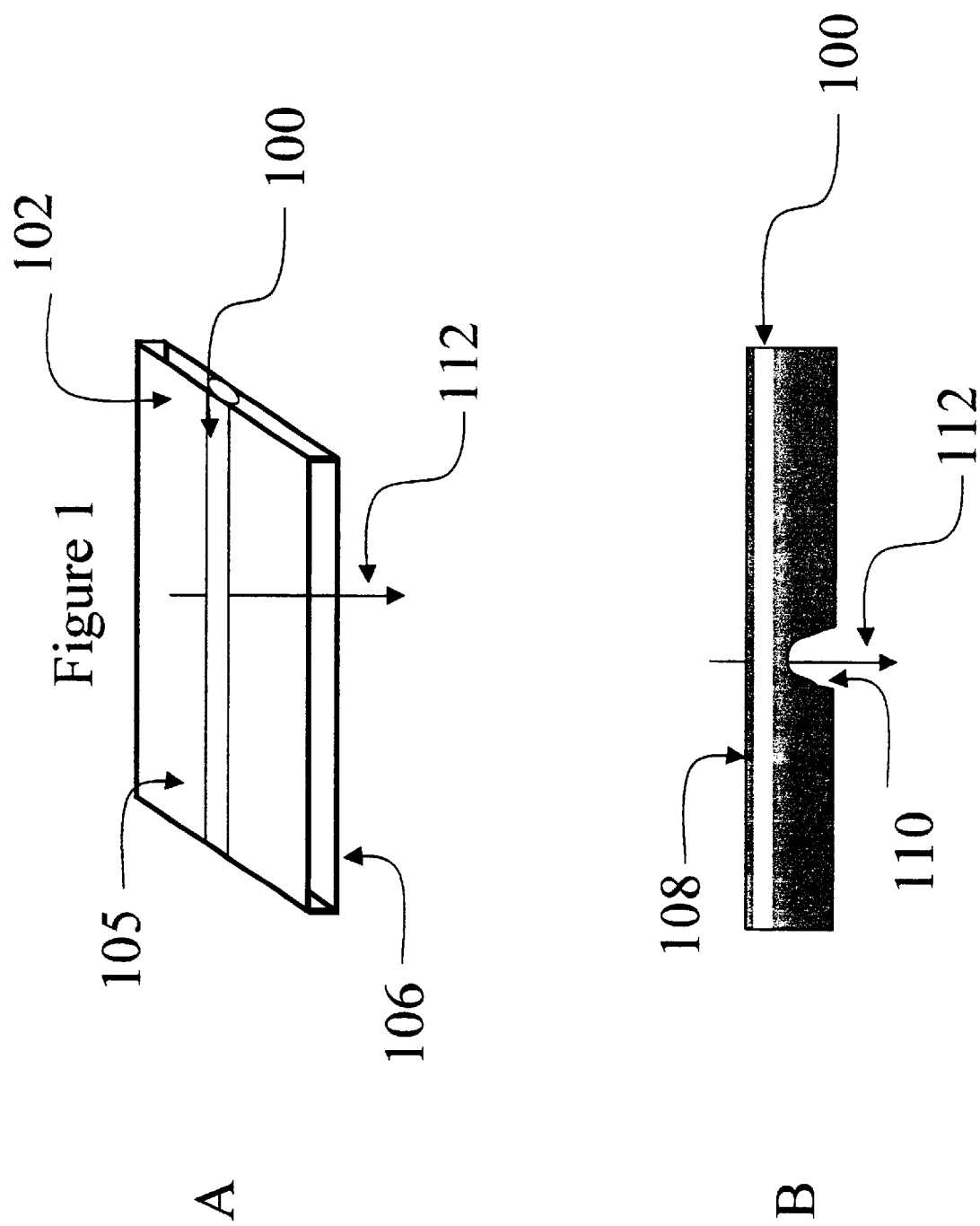

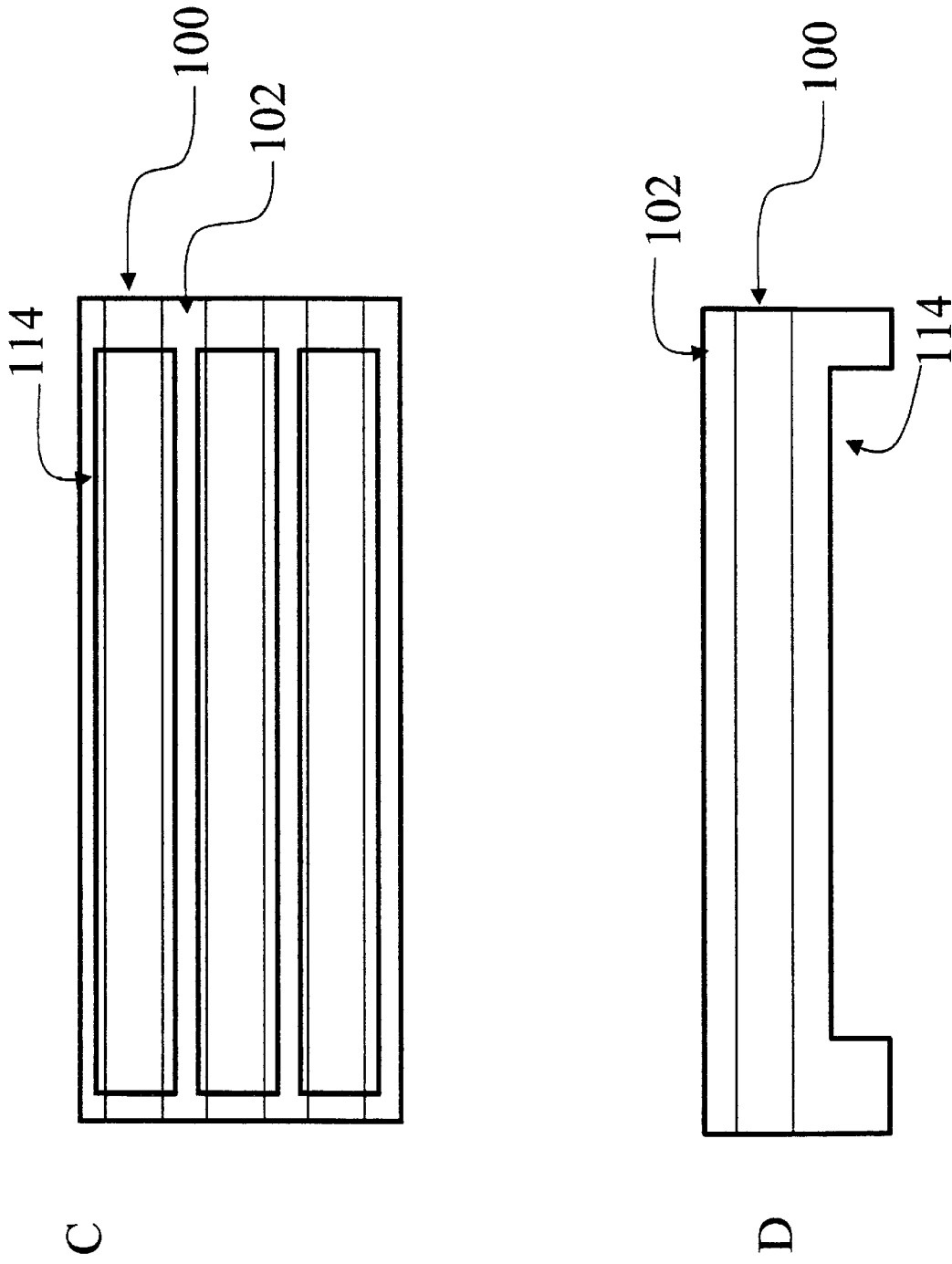

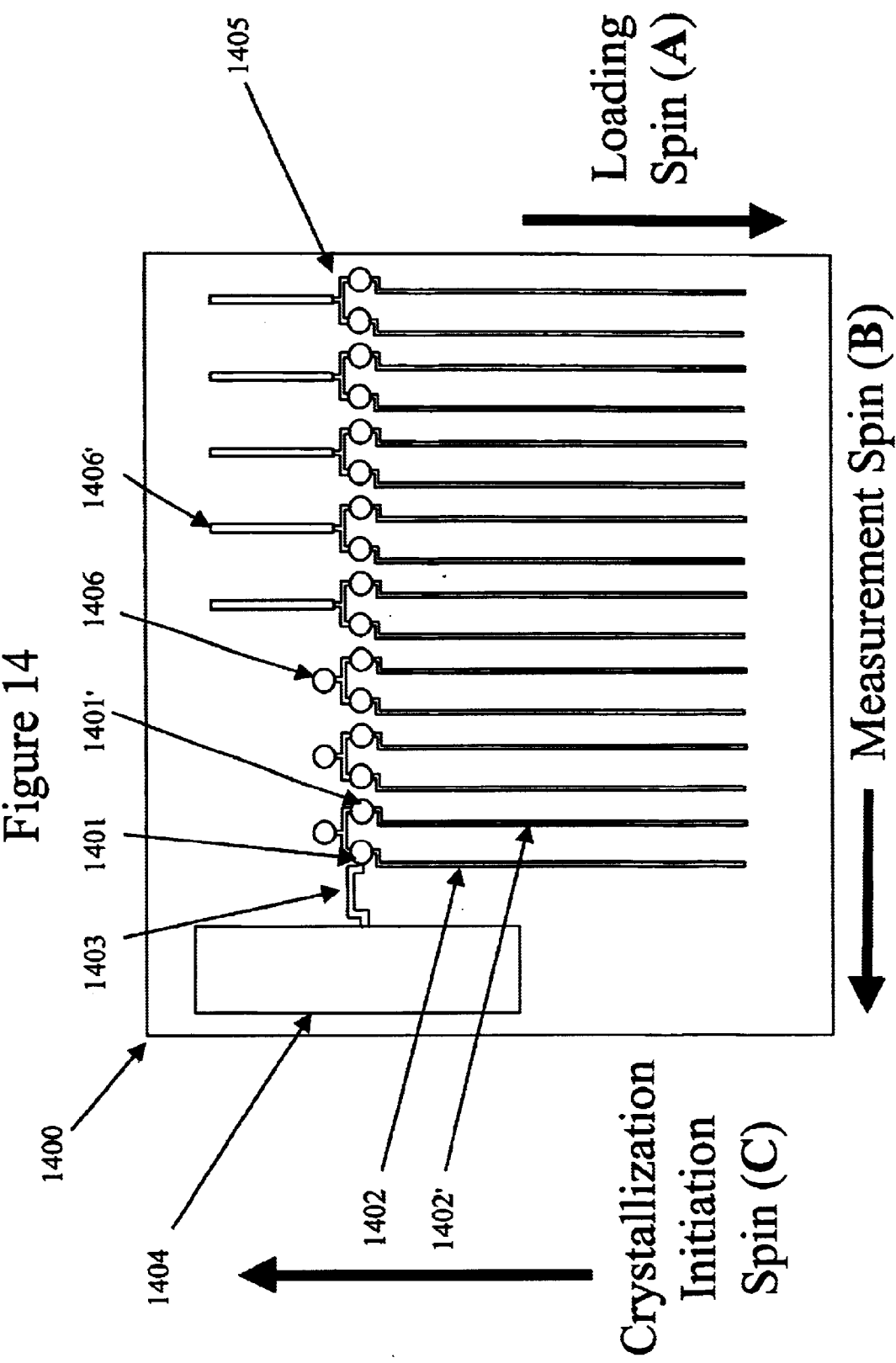

IN SITU CRYSTAL GROWTH AND CRYSTALLIZATION

BACKGROUND OF THE INVENTION

1. Field of the Invention

The present invention relates to devices and methods for performing crystallizations of molecules, and more specifically, to devices and methods for performing crystallizations of molecules in enclosed microvolumes.

2. Description of Related Art

Traditional methods for crystal growth and crystallization are highly labor intensive and require significant quantities of material to evaluate and optimize crystal growth conditions. Examples of these methods include the free interface diffusion method (Salemme, F. R. (1972) Arch. Biochem. Biophys. 151:533–539), vapor diffusion in the hanging or sitting drop method (McPherson, A. (1982) Preparation and Analysis of Protein Crystals, John Wiley and Son, New York, pp 82–127), and liquid dialysis (Bailey, K. (1940) Nature 145:934–935).

Presently, the hanging drop method is the most commonly used method for growing macromolecular crystals from solution, especially for protein crystals. Generally, a droplet containing a protein solution is spotted on a cover slip and suspended in a sealed chamber that contains a reservoir with a higher concentration of precipitating agent. Over time, the solution in the droplet equilibrates with the reservoir by diffusing water vapor from the droplet, thereby slowly increasing the concentration of the protein and precipitating agent within the droplet, which in turn results in precipitation or crystallization of the protein.

The process of growing crystals with high diffraction quality is time-consuming and involves trial-and-error experiment on multiple solution variables such as pH, temperature, ionic strength, and specific concentrations of salts, organic additives, and detergents. In addition, the amount of highly purified protein is usually limited, multi-dimensional trials on these solution conditions is unrealistic, labor-intensive and costly.

A few automated crystallization systems have been developed based on the hanging drop methods, for example Cox, M. J. and Weber, P. C. (1987) J. Appl. Cryst. 20:366; and Ward, K. B. et al. (1988) J. Crystal Growth 90:325–339. More recently, systems for crystallizing proteins in submicroliter drop volumes have been described including those described in PCT Publication Nos. WO00/078445 and WO00/060345.

Existing crystallization, such as hanging drop, sitting drop, dialysis and other vapor diffusion methods have the limitation that the material for analysis and the crystallization medium are exposed to the environment for some time. As the volumes of materials decrease, the ratio of surface area to volume ratio varies as the inverse of the radius of the drop. This causes smaller volumes to be more susceptible to evaporation during the initial creation of the correct mixture and during the initial period after the volume has been set up. Typical hanging drop plates can have air volumes of 1.5 milliliters compared to a sample drop size of 3–10 microliters. Moreover, typical methods expose the sample drop to the environment for a duration of seconds to minutes. Small variability in the rate that samples are made can cause significant variations in the production of crystals. Prior methods fail to reduce the problems of convection currents under 1 g such as those described in U.S. Pat. No. 4,886,646, without the large expenditure of resources or in methods that complicate crystal analysis.

SUMMARY OF THE INVENTION

A method is provided for determining crystallization conditions for a material, the method comprising: taking a plurality of different crystallization samples in an enclosed microvolume, the plurality of crystallization samples comprising a material to be crystallized and crystallization conditions which vary among the plurality of crystallization samples; allowing crystals of the material to form in plurality of crystallization samples; and identifying which of the plurality of crystallization samples form crystals.

A method is also provided for determining crystallization conditions for a material, the method comprising: taking a plurality of different crystallization samples in a plurality of enclosed microvolumes, each microvolume comprising one or more crystallization samples, the crystallization samples comprising a material to be crystallized and crystallization conditions which vary among the plurality of crystallization samples; allowing crystals of the material to form in plurality of crystallization samples; and identifying which of the plurality of crystallization samples form crystals.

These and other methods, devices, compositions and kits are described herein.

BRIEF DESCRIPTION OF FIGURES

FIG. 1A illustrates a card-like shaped device housing microvolumes with opposing faces.

FIG. 1B illustrates an embodiment of a card-like shaped device where the thickness of the overall card is reduced adjacent a region where x-rays will be incident in order to reduce the amount of material in the path of the x-rays.

FIG. 1C illustrates a bottom up view of an embodiment of a card-like shaped device where grooves have been created so that less material is present adjacent a region where x-rays will be incident.

FIG. 1D illustrates a cross sectional view of an embodiment of a card-like shaped device where grooves have been created so that less material is present adjacent a region where x-rays will be incident.

FIG. 4A illustrates a crystallization mixture performed within a lumen positioned between two dividers.

FIG. 4B illustrates a crystallization performed within a lumen where multiple crystallization conditions are simultaneously employed.

FIG. 4C illustrates a crystallization performed within a lumen where a series of crystallization agents are set up for crystallization against a series of substances to be crystallized.

FIG. 14 illustrates a device that is designed to move fluids within the device by centrifugal force.

FIG. 15A illustrates a repeating unit of the centrifugal array.

FIG. 15B illustrates a process for using a centrifugal device.

FIG. 15C illustrates the effect of centrifugal force on the samples that are loaded in the centrifugal device illustrated in FIG. 15B.

FIG. 15D illustrates what happens when the centrifugal force vector is changed such that the force now directs the excess crystallization agent and excess material to be crystallized toward the waste ports via the respective waste channels.

FIG. 15E illustrates each channel of the centrifugal device filled to point V, resulting in precise volume measurements.

FIG. 15F illustrates what happens when the centrifugal force vector has been altered to align in the direction shown.

FIG. 15G illustrates crystallization chamber filled with the combination of the material to be crystallized and the crystallization agent, or agents.

DETAILED DESCRIPTION OF THE INVENTION

Figure 2:
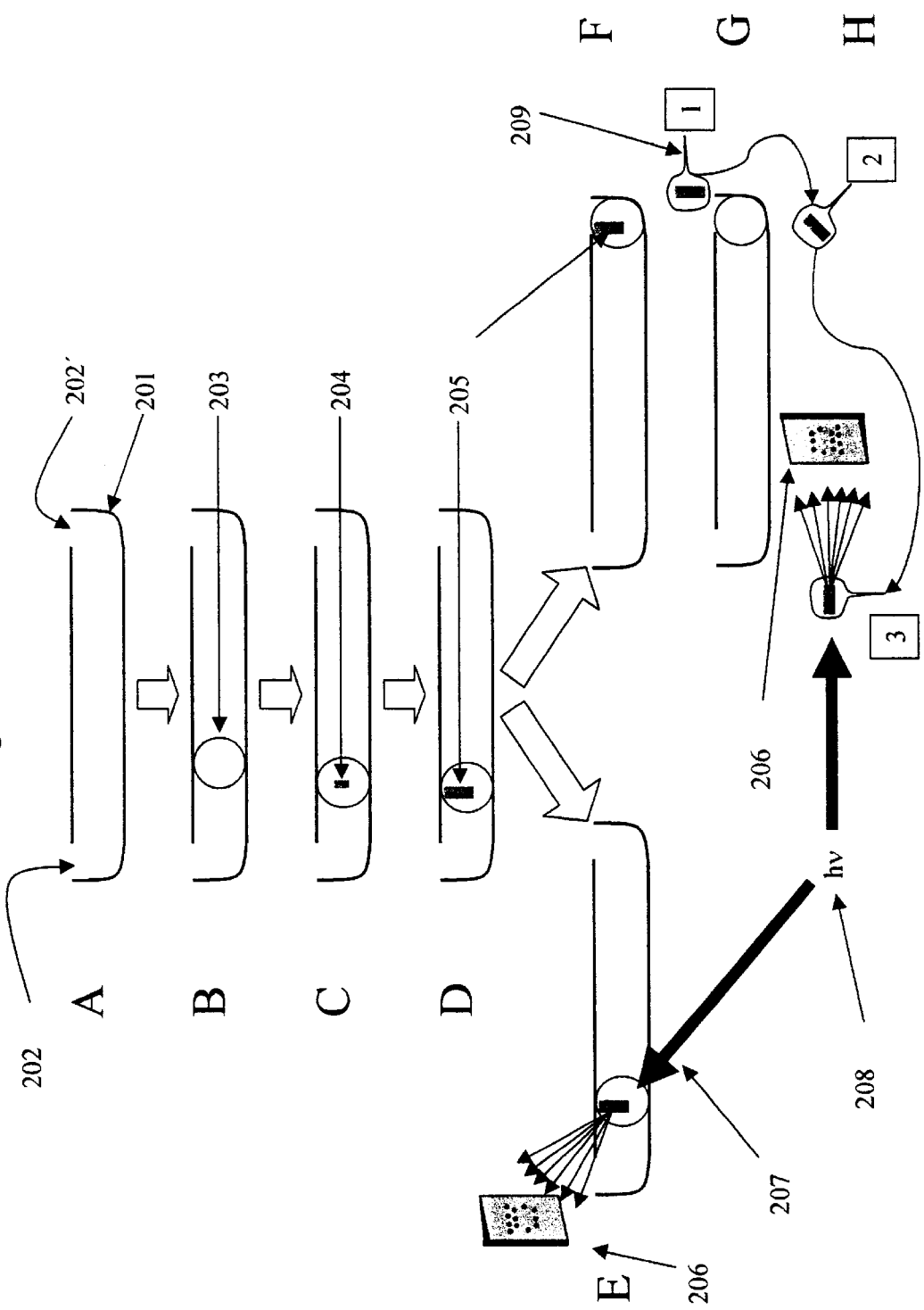
FIG. 2 illustrates the generalized use of a microsized lumen to form crystallization samples and perform crystallization.

The present invention generally relates to devices and methods for forming crystallization samples, transporting crystallization samples, and crystallizing materials therein, particularly in a microscale, high throughput manner. Distinguishing the present invention is the performance of the crystallizations in very small, substantially enclosed volumes formed by or within a substrate, referred to herein as an "enclosed microvolume".

A "crystallization sample", as the term is used herein, refers to a mixture comprising a material to be crystallized. The crystallization includes such other components in the mixture to cause or at least attempt to cause crystals of the material to be formed in the mixture.

According to the present invention, crystallization samples are formed, transported, and crystallization attempts conducted in enclosed microvolumes. These enclosed microvolumes comprise one or more lumens and optionally microchambers in fluid communication with the lumens. The lumens are enclosed within a substrate. When employed, microchambers are enclosed microvolumes defined within the substrate in fluid communication with the lumens. The lumens and microchambers provide an encased environment within which crystallization samples may be formed, and crystallization attempts performed and analyzed.

The term "lumen" as the term is used herein, refers to any elongated, enclosed volume formed at least partially by a substrate. The lumen preferably has a cross sectional diameter of less than 2.5 mm, preferably less than 1 mm and more preferably less than 500 microns. In one variation, the lumen has a cross sectional diameter between 0.1 microns and 2.5 mm, preferably between 0.1 microns and 1 mm, and preferably between 0.1 and 500 microns. Aside from openings in the lumen, most typically adjacent the proximal and distal ends of the lumen, the lumen provides an enclosed environment in which to form, transport, conduct, and optionally analyze crystallizations.

Mass flow may be reduced by controlling the length of the crystallization volume within the microlumens. This serves to reduce the forces driving convection currents within the crystallization condition. By minimizing the length of the crystallization volume within the microlumens, facile control of the degree of convection currents within the microlumen is controlled.

In certain instances, it may be desirable for the lumen to be in fluid communication with one or more microchambers. A "microchamber", as the term is used herein, refers to a volume in fluid communication with a lumen that has a larger cross sectional area than the lumen.

By forming crystallization conditions and performing crystallizations within the small, relatively sealed volumes defined by the enclosed microvolumes of the lumens and microchambers, a variety of different advantages are provided.

One advantage provided by conducting cystallizations in enclosed microvolumes is that it facilitates parallel screening of many materials at once or a material in many conditions at once, or a combination thereof.

A further advantage provided by the small volumes associated with performing crystallizations in enclosed microvolumes is that it enables the conservation of the material to be crystallized, thereby enabling greater numbers of crystallization conditions to be sampled using a given amount of material. By achieving higher densities of crystallization conditions, advancements in crystal analysis are obtained.

A further advantage provided by performing crystallizations according to the present invention is a reduction in evaporation during the preparation and performance of the crystallization. As a result, crystallization conditions can be more precisely controlled and remain stable for longer periods of time. Crystallizations can also be conducted over a wider range of temperature conditions since losses due to evaporation are significantly curtailed.

A further advantage provided by performing crystallizations according to the present invention is a further reduction in the space requirements for performing crystallizations. More specifically, the present invention allows multiple crystallizations to be performed in a denser format. This allows the device within which the crystallizations are performed to be smaller and allows more crystallizations to be performed in a single device. For example, when in situ crystallizations are performed in a thin cassette or card, the crystallizations may be densely packed, allowing for rapid and efficient analysis of the crystallization conditions.

A further advantage provided by performing crystallizations according to the present invention is the more rapid equilibration times that may be achieved by further reducing crystallization volumes.

As will be evident from the foregoing description of the operation of the devices of the present invention, a further advantage provided is simplified material handling.

1. Materials to be Crystallized

While problems associated with crystal growth addressed by the present invention are of particular interest for proteins and other biomolecules, it is a general problem of all crystal forming materials. The materials to be crystallized may be any substance capable of crystallizing or co-crystallizing, for example a biomolecule, a virus, a protein, a peptide, a nucleoside, a nucleotide, ribonucleic acids, deoxyribonucleic acids, a ligand, a drug molecule, a biologically active substance, a pharmacologically active substance, an enzyme substrate, polymers, a gas, an ion, or an uncharged substance, or mixtures or composites of combinations thereof.

The materials to be crystallized may be any material for which a crystal structure is needed. Determining high-resolution structures of materials by a high-throughput method such as the one of the present invention can be used to accelerate the analysis of materials, especially drug development.

The material to be crystallized may also be a molecule for which a crystalline form of the molecule is needed. For example, it may be desirable to create a crystalline form of a molecule or to identify new crystalline forms of a molecule. In some instances, particular crystalline forms of a molecule may have greater biological activity, dissolve faster, decompose less readily, and/or be easier to purify.

The material to be crystallized may also be a combination of substances for the production of co-crystals. The co-crystals can comprise any two of a small molecule, a drug, a ligand, a substrate, an inhibitor, a guest chemical, protein, nucleotide, or a protomer. The substances can be a plurality of small molecules, drugs, ligands, substrates, inhibitors, guest chemicals, proteins, or a protomers.

The material to be crystallized is preferably a macromolecule such as a protein but may also be other types of macromolecules. The molecule preferably has a molecular weight of at least 500 Daltons, more preferably at least 1000 Daltons, although smaller molecular weight molecules may also be crystallized.

2. Construction of Enclosed Microvolumes

Construction of lumens and microchambers leading to and from lumens is well known in the art. For example, U.S. Pat. Nos. 5,126,022; 5,296,114; 5,180,480; 5,132,012; and 4,908,112 are examples of references detailing the design and construction of lumens and microchambers in a substrate. Other examples of references include Harrison et al., "Micromachining a Miniaturized Capillary Electrophoresis-Based Chemical Analysis System on a Chip," Science (1992) 261:895; Jacobsen et al., "Precolumn Reactions with Electrophoretic Analysis Integrated on a Microchip," Anal. Chem. (1994) 66: 2949; Effenhauser et al., "High-Speed Separation of Antisense Oligonucleotides on a Micromachined Capillary Electrophoresis Device," Anal. Chem. (1994) 66:2949; and Woolley & Mathies, "Ultra-High-Speed DNA Fragment Separations Using Capillary Array Electrophoresis Chips," P.N.A.S. USA (1994) 91:11348. These examples are only intended to be illustrative. Enclosed microvolumes may be formed by any available method and used in conjunction with the present invention.

The enclosed microvolumes may be formed in any substrate within which microvolumes may be formed. Examples of suitable substrates include, but are not limited to glass, fused silica, acrylics, thermoplastics, and the like. The various components of the integrated device may be fabricated from the same or different materials, depending on the particular use of the device, the economic concerns, solvent compatibility, optical clarity, color, mechanical strength, and the like.

For applications where it is desired to have a disposable device, due to ease of manufacture and cost of materials, the device will typically be fabricated from a plastic. For ease of detection and fabrication, the entire device may be fabricated from a plastic material that is optically transparent, as that term is defined above. Particular plastics finding use include polymethylmethacrylate, polycarbonate, polyethylene terepthalate, polystyrene or styrene copolymers, and the like.

The substrate comprising the enclosed microvolumes may be in any form, e.g., a tube, a card, a chip or a block. The substrate is preferably in the form of a card. The card preferably has a size less than 12 cm×8.5 cm.

The enclosed microvolumes may be formed by any process by which an enclosed lumen or chamber may be created in a material. For example, the shape of the substrate and the enclosed microvolumes may be formed by thermoplastic injection molding, micromolding, punching, milling, any solid free form technology, such as three dimensional printing, or other types of manufacturing technologies for plastics, such as micromolding, embossing, laser drilling, extrusion, injection, or electron deposition machining, glass or silicon, conventional silicon processing technology, such as photolithography, deep reactive ion or wet etching, electron beam machining, micromachining, electro-discharge machining, reaction injection molding.

It is noted that the substrate comprising the enclosed microvolume may be formed of a single material, such as a block or a card. Alternatively, one or more materials may be brought together to form the enclosed microvolume. This typically involves having a portion of the microvolume be formed by a first substrate (e.g., photolithography on a surface of the first substrate). A second substrate is brought together with the first substrate to complete the definition of the enclosed microvolume. The act of combining the first and second substrates can cause the material to be crystallized to be enclosed. The act of combining can also cause mixing to occur.

The substrate is preferably optically clear, transparent, translucent or opaque. The substrate is preferably formed of a material which allows for various spectroscopic analyses (e.g., Raman, UV/VIS, IR or x-ray spectroscopy, polarization, fluorescent, and with suitable designs, x-ray diffraction) to be performed in situ.

In order to optimize the performance of the substrate for performing in situ x-ray diffraction, the number of electrons in the substrate material in the path of the x-ray beam as it passes through the substrate, prior to interacting with the crystallization conditions should be minimized.

The number of electrons can be reduced by choosing materials having a low atomic number (Z), or a low density. Examples of materials which are preferably used for reducing the number of electrons in the substrate material include low density plastics such as polystyrene, polyethylene, other carbon based polymers. Silicon materials, such as silicon wafers, glass, including borosilicate and soda glass, and aerogels can be suitable materials. Optically opaque materials that are suitable include Berylium, plastic films and plastics. The key parameter R, is that the ratio of the number of electrons within the sample to be tested, that is the crystal or the contents of the microlumen should contain at least as many electrons within the area of the x-ray beam as the sum of the electrons contained in the support material and the lid, or sealing material. Preferably, the ratio of the electrons should be at least three, more preferably five and optimally more than ten.

$$R = \frac{\sum [e^-]_{Crystal}}{\sum [e^-]_{Cassette}},$$

where the number of electrons in the x-ray beam, $[e^-]$, is calculated by multiplying the density of the material in grams, by thickness of the material and the area of the x-ray beam at the microlumen, which gives the mass in grams, X, of the microlumen material in the x-ray beam. This can be converted into the number of electrons by multiplying the mass in grams by Avagadro's number, N, and dividing by the molecular weight of the material, MW. i.e.,. $[e^-]=X*N/MW$ The number of electrons in the path of the incident x-rays can also be reduced by minimizing the mass of material in the path. Accordingly, the substrate enclosing the channels preferably contains as little material as possible in the direction of the path of the x-rays. As illustrated in FIG. 1A, the device housing the microvolumes 100 will most commonly have a card-like shape 102 with opposing faces 104 and 106. Walls 108, 110 (shown in FIGS. 1B and 1C) adjacent the opposing faces define a portion of the microvolume. X-rays 112 will typically traverse the card substantially perpendicular to the opposing faces in order to minimize the path length across the card, that path length being defined largely by the thickness of walls 108, 110. It is desirable for the card to have sufficient thickness so that it will be sufficiently rigid for necessary handling. However, by reducing the amount of material forming the walls 108, 110 adjacent a portion of the microvolume where x-rays will be incident, one can reduce the amount of mass in the path of the x-rays.

FIG. 1B illustrates an embodiment where the thickness of the overall card is reduced adjacent a region where x-rays will be incident in order to reduce the amount of material in the path of the x-rays.

FIGS. 1C and 1D illustrate an embodiment where less material is present adjacent a region where x-rays will be incident in order to reduce the amount of material in the path of the x-rays. This may be accomplished by forming a card as shown in FIG. 1C with grooves 114 on one or both sides adjacent where x-rays will be incident. If the microvolume is closely adjacent one face of the card, a groove is preferably formed adjacent the opposite side of the card as shown in the cross sectional view provided by FIG. 1D. It is noted that the card may be formed with the grooves or may be formed without the grooves and then material may be removed from the card to create the grooves.

As will be illustrated herein, crystallization conditions may be formed by delivering different components to a single lumen or by delivering different components to a given lumen or microchamber from multiple different lumens. In this regard, the multiple different lumens are preferably interconnected.

The cross sectional shape of the lumen may stay the same or may vary along the length of the lumen. Optionally, the lumen may be connected to one or more chambers to which material from the lumen is delivered or from which material is delivered to the lumen. It is noted that crystallizations may also be performed in the chambers after material is delivered via the lumen to the chamber.

The lumen may have a variety of cross sectional geometries. For example, the cross-sectional geometry of the lumen may be circular, semi-circular, ovoid, "U" shaped, square, or rectangular, or one or more combinations thereof. Preferably, the cross sectional area of the lumen is small relative to the length of the lumen. This serves to reduce convection currents within liquids passing within the lumen. Convection currents may be further reduced by the use of thixotropic agents, such as silica gel, agarose, other polysaccharides and polymers.

3. Layout and use of Microsized Lumens for Performing Crystallizations

A generalized use of a microsized lumen to form crystallization samples and perform crystallization attempts is illustrated in regard to FIG. 2. As shown in step A of FIG. 2, an enclosed lumen 201 is provided such that the lumen 201 has at least one opening 202A adjacent a first end of the lumen and at least one opening 202B adjacent a second end of the lumen. A crystallization experiment 203 is introduced into the lumen 201 via one of the openings, as shown in step B. This material may be a preformed crystallization experiment, consisting of a material to be crystallized and one or more crystallization agents, or it may be a material to be crystallized that will undergo a diffusional experiment, wherein material will be transferred either through vapor or liquid diffusion. Step C of the figure shows the crystallization experiment proceeding such that a portion of the material either crystallizes into a crystal 204 or a plurality of crystals, microcrystals, needles, precipitates or other solids, or the material remains in solution.

If a crystal forms, as shown in step D of the figure (shown as 205), then the crystal may be examined in situ, for example, as shown in steps E–H. Examination may be performed by any available method, including, but not limited to spectroscopically, visually, or if the crystallization channel is suitably designed, by direct exposure of x-rays. As shown by the arrows leading from step D, the crystal or crystallization mixture may be harvested from the lumen.

Steps E–H show different processing steps that may be performed on the crystal or crystallization mixture. Step E illustrates a crystal being examined within a lumen via x-ray diffraction by using an x-ray source 208 suitable for diffraction experiments, which is suitably focused and collimated to pass through the material to be examined. The diffracted x-rays can then be examined through the use of a suitable x-ray detector 206, which can be x-ray film, one dimensional x-ray detectors, two dimensional (area) detectors, or an electronic x-ray detector or scintillator. Alternatively, as shown in step F, the crystal 205 can be manipulated within the crystallization channel. This enables the harvesting of the crystal as shown in step G, wherein the crystal containing crystal experiment is brought to an outlet of the crystal channel.

As shown, the crystal can be harvested into an intermediate device, or may be harvested directly with a mounting suitable for x-ray diffraction. This mounting can be a loop 209, as shown in step G, or it can be a capillary suitable for x-ray mounting, or a fiber, or a spatula. These techniques for harvesting and manipulating crystals are widely known. Once the crystal is harvested, the crystal can then be transported to an x-ray diffraction experiment shown as step H where the crystal can be mounted in a position to facilitate the diffraction experiment. It should be appreciated that the material to be analyzed may not be a single crystal. The material may be twinned crystals, or a plurality of crystals grouped together, or a number of loose crystals, or a precipitate, which can then be examined for crystalline elements.

The crystallization drop 203 can be created within the microlumen, or it can be mixed outside of the channel and introduced into the channel. The actual method for loading the channels will vary depending upon the necessities of the experiment. A crystallization mixture can be formed by the use of a syringe, such as a Hamilton syringe, or via a parallel robotic system such as the Tecam, wherein the relevant volume of material to be crystallized is drawn up into the syringe and then the relevant volume of the crystallization agent can be drawn up. The material may be dispensed directly into the loading port 202, or may be dispensed into or onto an intermediate surface or container for mixing. The material can be applied to the inlet port under pressure from the syringe, or may be loaded onto the upper surface of 201, such that the droplet covers the inlet port 202. The droplet can then be loaded into the microlumen by the application of a pressure difference to 202 and 202', either through pressure at 202 or through vacuum at 202'. Similarly, after the crystal has grown, the application of a pressure difference, either directly, or indirectly through a pressure transfer fluid, such as mineral oil or buffer, the crystal can be moved to the outlet port 202', for harvesting as shown above in steps 1–3 of FIG. 2G and 2H.

Figure 3:
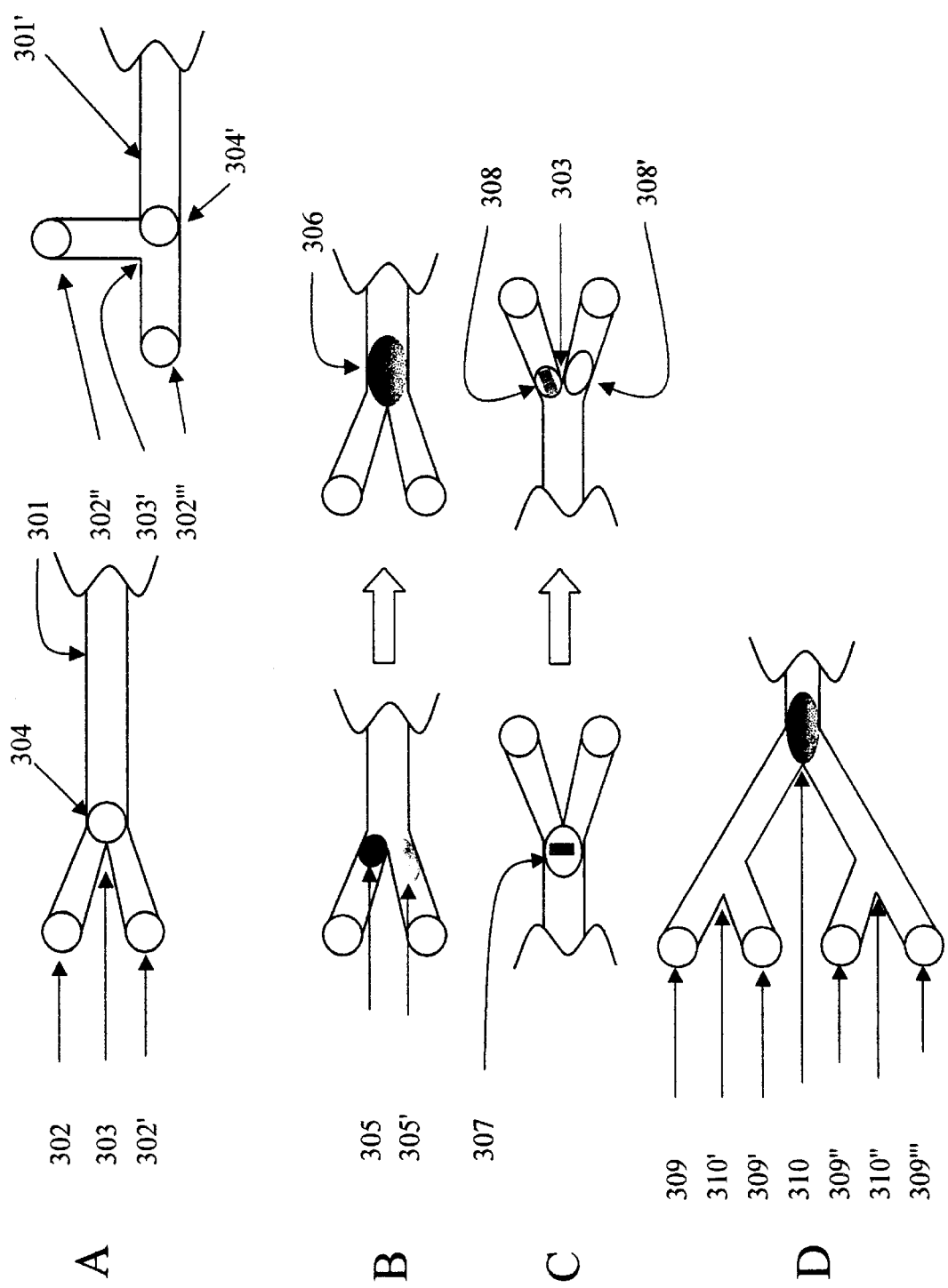
FIG. 3A illustrates various interconnections that may be formed between different lumens.
FIG. 3B illustrates how two sub-lumens extending from and joining with a main lumen may be used to effect mixing within the main lumen.
FIG. 3C illustrates the use of a dividing feature to separate a crystal containing crystallization experiment into two portions.
FIG. 3D illustrates different combinations of single and double ports that may be combined for complex mixing, separation, diffusion and purifications.

It is noted that a given lumen may have multiple lumens interconnecting with it or extending from it. For example, as shown in FIG. 3A, a lumen 301 may have two inlet ports 302A and 302B and a junction 303 that may form an acute, perpendicular or obtuse intersection. A perpendicular intersection is illustrated in FIG. 3A where the intersection 304 of channels 302C and 302D is formed perpendicularly.

FIG. 3B illustrates how two sub-lumens extending from and joining with a main lumen may be used to effect mixing within the main lumen. Material 305A in one sub-lumen of the main lumen and material 305B in the second sub-lumen extending from the main lumen are joined and mixed together into a single volume 306 by the geometry of the interconnecting channels. Depending upon the particular application, the lumens and sub-lumens can be designed to effect differing levels of mixing and the alteration of the interface between the two substances. Obviously, the lumens may possess both combining features or dividing features or a combination thereof, or depending on the absolute and relative flows combining features that function as dividing features under altered fluid flows.

FIG. 3C illustrates the use of a dividing feature 303 to separate a crystal containing crystallization experiment 307 into two portions 308A and 308B. It should be understood that the relative volumes in 308A and 308B can be readily attained by, suitable design or practice, by achieving differential fluid flows.

It should also be appreciated that different combinations of single and double ports may be combined for complex mixing, separation, diffusion and purifications as illustrated in FIG. 3D. For example, as shown, ports 309A and 309B meet at junction 310A. Similarly, ports 309C, 309D meet at junction 310B. The sub-lumens from junctions 310B and 310C can intersect at 310A.

To generate the result shown in FIG. 3A, one might apply a sample to inlet port 302, block port 302', and apply a positive pressure difference between port 302 and the pressure within 301. This can be effected by applying a small vacuum at 301, by the removal of material from 301 hydraulically, or by the application of pressure at 302, or by the application of centrifugal force with a component along 301. The droplet can be brought to a stop at 303 by removing the motive force at such a time that the material comes to rest at 304. PID (Proportional-Integrating-differential) methods and/or controllers are very effective for optimizing fluid delivery accounting for hysteresis effects within the fluid transfer mechanisms and the microlumens. In FIG. 3B, material can be applied at 302 and 302' and then individually advanced as described above, or may be advanced in tandem by the application of pressure differential across both fluids simultaneously to yield the combined mixture 306 at the union of the two microlumens. FIG. 3C is constructed by inducing the material assembled in a crystallization bolus 306 to crystallize. Pressure can then be applied to the interior of the microlumen 301 to force the crystal containing bolus 307 along the microlumen 301 to the intersection 303. This pressure can be applied hydraulically to port 302 or 302', while sealing the other, or to both ports 302 and 302' simultaneously. The hydraulic pressure can be applied directly via syringe or syringe pump or via a hydraulic transfer fluid such as water or mineral oil using a fluid filled syringe or syringe pump, with or without a connecting manifold to facilitate the application of the hydraulic pressure to the ports 302 and 302'. At harvest, by modulating the pressure difference between two outlet ports, the unwanted crystallization liquor can be preferentially forced into the waste passage as bolus 308', while concentrating the crystal in a desired amount of crystallization liquor in bolus 308'. The pressure can be modulated by differential pumping of two syringe pumps connected to the respective outlet ports. This can be done under manual control with a simple joystick controller, or it can be accomplished with computer vision software, such as that provided by Keyance.

The methods and the devices of the present invention will now be described with regard to the following figures.

Figure 4:
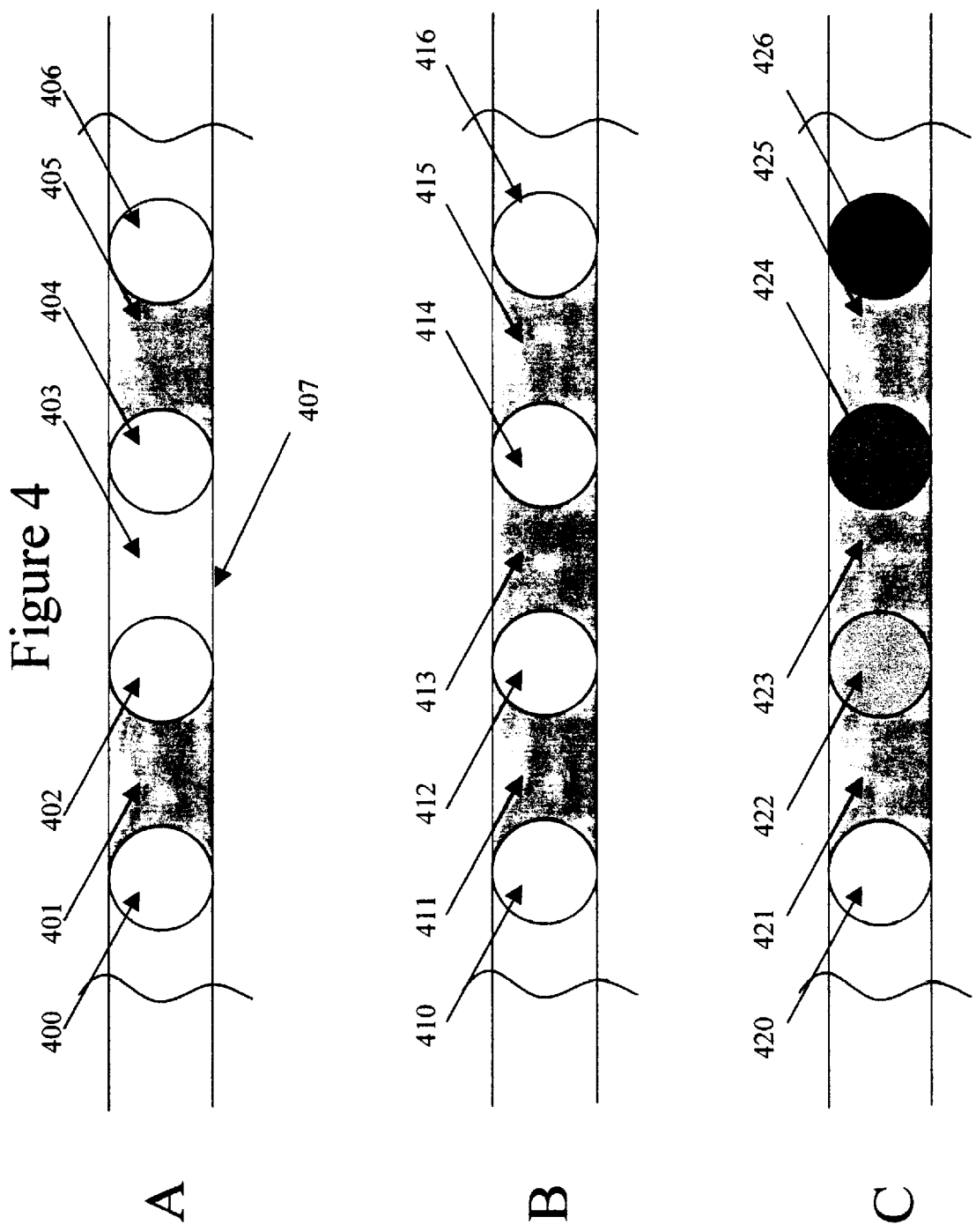
FIGS. 4A–4C provide several embodiments of performing crystallizations within a lumen.

FIGS. 4A–4C provide several embodiments of performing crystallizations within a lumen. It should be recognized that depending upon the differing surface energies of the solutions and the enclosure the actual interfaces may be convex, concave, flat or with elements of all three. For illustrative purposes, the interfaces are shown to be spherical.

FIG. 4A illustrates a crystallization mixture 401 formed within a lumen 403 positioned between two dividers 400, 402. The lumen 403 is formed at least partially by a substrate 407 and enclosed therein. The dividers 400, 402 may be semipermeable gases or liquids, semipermeable gels or permeable gels, or thixotropic liquids, or immiscible and impermeable liquids or beads. As a result, the interface formed between a crystallization and a divider may be a liquid/liquid, liquid/gas interface, liquid/solid or liquid/sol-gel interface. In some instances, the interface may also be a membrane, gel, frit, or matrix to modulate or alter the diffusion characteristics.

The dividers can be impermeable, semipermeable or permeable. For example, semipermeable substances such as air, oil, solvent, gel and beads can be used as dividers. The dividers can also be physical constructions, such as a narrow pore, a thin passage, a frit or sintered beads or powders.

In crystallizations performed within lumens according to the present invention, there may be one or multiple crystallization conditions, either related or unrelated in a given lumen. The dividers serve to separate and optionally isolate the different crystallization conditions. For example, a second crystallization condition, potentially one of many, is illustrated by dividers 404, 406 surrounding crystallization 405. The dividers and the gap 403 may optionally be omitted.

Alternatively, the substance to be crystallized can be element 401, with 400 and 402 being crystallization agents, either identical or different. In this instance, element 403 functions as a barrier between one condition and the next. As illustrated in FIG. 4B, element 403 can be omitted for a series of crystallizations.

By positioning barrier material on opposing sides of a crystallization within the microlumen, the crystallization may be encased and its length thereby controlled. Examples of barrier materials that may be used include, but are not limited to immiscible solvents or solids. The barrier materials may form a complete or partial barrier. Complete barriers prevent the crystallization from traversing the barrier material. Partial barriers limit the rate at which components of the crystallization traversing the barrier material. Examples of partial barrier materials include, but are not limited to polymers or solvents that allow for diffusion. Diffusion within the crystal conditions can be further modified by the use of thixotropic agents, gels or sols to prevent convective movements of the solutions.

As yet an alternative method, the substance to be crystallized may be elements 400, 402, 404, and 406. In this instance, elements 401 and 405 may be crystallizing agents. Element 403 meanwhile may be a barrier or can be another crystallization agent.

In all cases, the crystallization agent can be mixed prior to attempting to perform the crystallization within the lumen or can act in situ, with no prior mixing.

FIG. 4B illustrates a crystallization performed within a lumen where multiple crystallization conditions are simultaneously employed. As illustrated, elements 411, 413, and 415 can be crystallization conditions, either premixed with crystallization agents or not. If elements 411, 413, and 415 are premixed, then elements 410, 412, 414, 416 may optionally be a semipermeable gas or liquid, a semipermeable gel or permeable gel, a thixotropic liquid, an immiscible liquid, an impermeable liquid or bead, or a crystallization agent.

In the instance where 411, 413, and 415 are not premixed, then minimally, 412 and 414 are crystallization agents and the termini, 410 and 416 are a barrier (e.g., either a bead, an impermeable substance or a gas bubble).

In the instance that the crystallization is rapid, it is not necessary to have impermeable termini. Instead, diffusion from the termini can be used as an additional crystallization agent.

FIG. 4C illustrates a crystallization performed within a lumen where a series of crystallization agents are set up for crystallization against a series of substances to be crystallized. In FIG. 4C, the crystallization agents are shown as elements 420, 422, 424, and 426. The crystallization attempts comprising substances to be crystallized are shown as elements 421, 423, and 425. These crystallization attempts may or may not be identical.

The sequential crystallizations can be formed in the microlumen by the sequential addition of the materials in inverse order. Thus, sample 406 is loaded into the microlumen, followed by 405, followed by 404 and so forth. Obviously, the microlumen can be loaded from right to left or left to right. The individual crystallizations may be made on the cassette by using a manifold such as the one show in FIG. 3D, and then varying the relative pressures in the manifold individually or in parallel to achieve the desired mixing. For instance, barrier material might be loaded via 309, protein via 309', semipermeable material via 309'', and a crystallization agent via 309'''. The alternating volumes of fluid can be easily made outside of the microlumen by the sequential loading of a syringe pump. To do this, the syringe loads the first sample volume from the source of the first material 400 by creating a pressure differential. The second material 401 is then loaded by the same method. Then the next material 403 is loaded until either the volume limit is reached upon the syringe or the desired contents of the microlumen have been loaded. The syringe pump can then unload the contents into the inlet port on the microlumen. FIG. 4C might be conveniently constructed through the use of a Tee as shown in FIG. 3A, wherein a series of crystallization conditions could be injected into the microlumen, alternating with suitable injections of material to be crystallized. It will be appreciated by those skilled in the art, that complete droplets can be made by small bursts of differential pressure.

FIGS. 5A–5D illustrate crystallizations being performed within lumens where one or more of the elements of the crystallization experiment change along a length of the lumen. As will be explained, the change can occur discretely or continuously, and need not be changed in a simple linear method.

Figure 5:
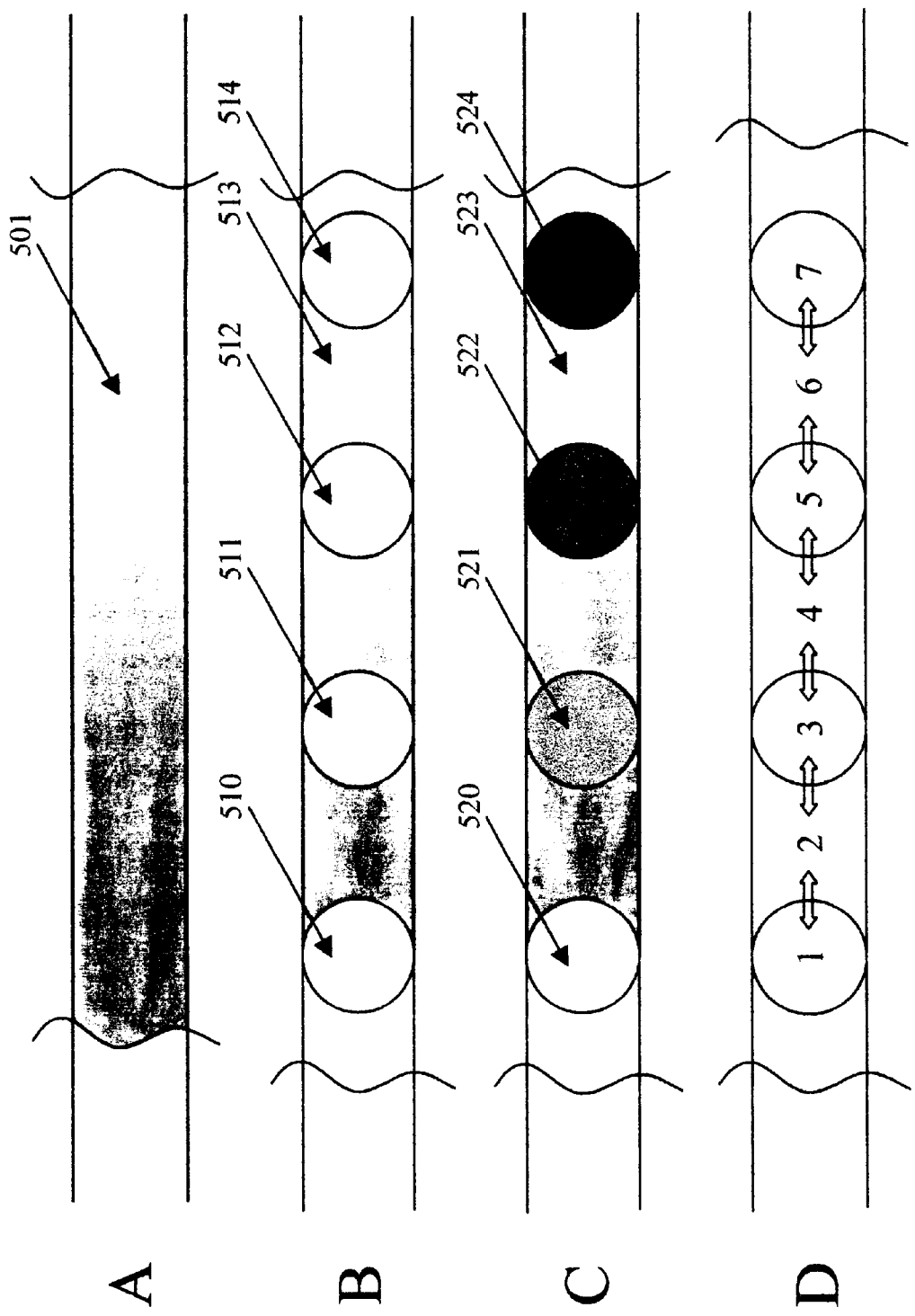
FIG. 5A illustrates a crystallization performed within a lumen where one or more of the elements of the crystallization experiment change along a length of the lumen. The change can occur discretely or continuously, and need not be changed in a simple linear method.
FIG. 5B illustrates a crystallization performed within a lumen where a series of substances to be crystallized are in a single gradient.
FIG. 5C illustrates a crystallization performed within a lumen where a series of crystallization agents can be assayed against a substance to be crystallized.
FIG. 5D illustrates diffusion between various elements in a crystallization performed within a lumen.

FIG. 5A illustrates a lumen 501 where the crystallization condition is different across the lumen.

FIG. 5B illustrates a series of substances to be crystallized, shown as elements 510, 511, 512, and 514. These substances are present in a single gradient 513 such that the different elements are exposed to different crystallization conditions.

FIG. 5C illustrates an alternative to the embodiment shown in FIG. 5B. In this embodiment, a series of different crystallization agents 520, 521, 522, and 524 are present within the lumen and are used to provide different conditions for crystallizing substance 523 present across the lumen.

FIG. 5D illustrates diffusion between the various elements in an in situ crystallization. Termini 1 and 7 share a single interface for diffusion. Each of the remaining portions of the in situ crystallization share at least two distinct interfaces for diffusion. Thus, a single substance to be crystallized, present across the lumen, can be assayed against two or more crystallization agents simultaneously. For example, substance 2 is shown to share two separate interfaces, which can cause crystals to grow either near the 1 to 2 interface or the 2 to 3 interface. Crystals growing in the center of 2 are indicative of a substance that requires aspects of both 1 and 3 to crystallize.

The gradient shown in FIG. 5A can be created by using a "Tee" shown in FIG. 3A together with a series of mixing baffles downstream. Initially all of the input flow comes from one of the ports, for example 302". The flow in the second port 302'" is increased, usually with a corresponding decrease in the amount of material flowing in at 302". The relative injection volumes, the total volume injected and the rate at which they change will affect the final gradient produced. Gradients may be formed off chip by similar means. The addition of a series of crystallization agents can be effected via the use of a "Tee" as described above, or may be individually loaded in an inlet port.

Figure 6:
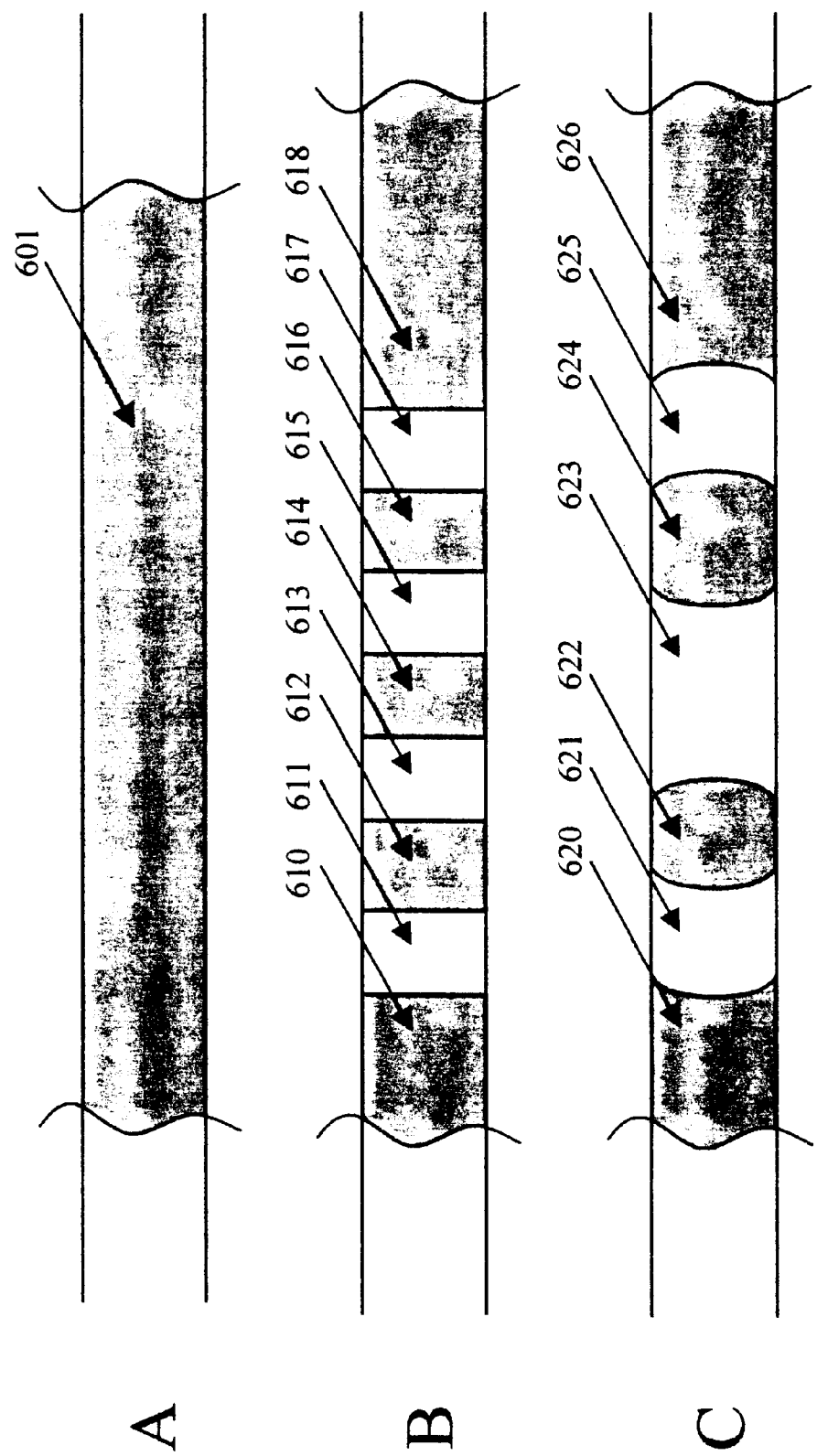
FIG. 6A illustrates a crystallization performed within a lumen where a single crystallization condition occupies an entire crystallization space.
FIG. 6B illustrates multiple crystallizations being performed within a lumen where dividers are used between the crystallizations, the dividers being shown to have planar surfaces adjacent the crystallizations.
FIG. 6C illustrates multiple crystallizations being performed within a lumen where dividers are used between the crystallizations, the dividers being shown to have curved, convex surfaces adjacent the crystallizations.

FIG. 6A illustrates a crystallization performed within a lumen where a single crystallization condition 601 occupies an entire crystallization space.

FIG. 6B illustrates multiple crystallizations being performed within a lumen where dividers 611, 612, 615, 617 are used between the crystallizations 610, 612, 614, 616, and 618. The dividers are shown in the figure to have planar surfaces adjacent the crystallizations.

FIG. 6C illustrates multiple crystallizations being performed within a lumen where dividers 621, 623, 625 are used between the crystallizations 622, 624. The dividers are shown in the figure to have curved, convex surfaces adjacent the crystallizations 622, and 624 that have complementary concave surfaces. The actual shape of the meniscus dividing the samples is a function of the surface tension at the interface and the surface of the microlumen.

Figure 7:
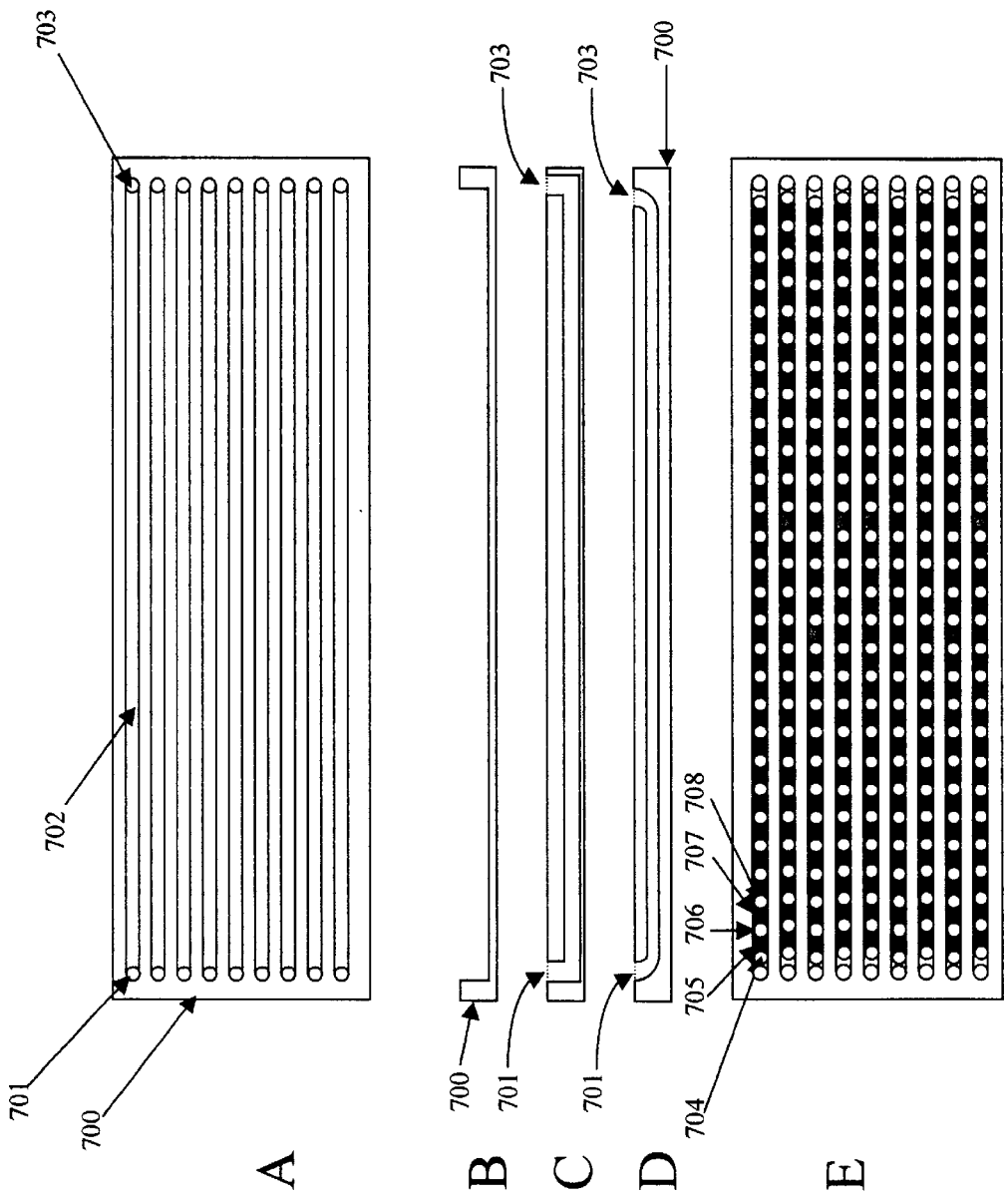
FIG. 7A shows a device for performing a series of crystallizations within a series of lumens where each lumen comprises a loading and unloading port and a lumen body interconnecting the ports.
FIG. 7B shows a cross section of a device for performing a crystallization within a lumen where the lumen is not enclosed.
FIG. 7C shows a cross section of a device for performing a crystallization within a lumen where the lumens are rectangular in shape.
FIG. 7D shows a cross section of a device for performing a crystallization within a lumen where the lumens are curved or tubular in shape.
FIG. 7E shows a device for performing crystallizations within a series of lumens where the lumens are loaded with samples that are separated by divider or modifier segments. It should be appreciated that each discrete sample may have conditions which are potentially unique and unrelated to adjacent samples. The dividers or modifiers positioned between the samples can be permeable, semi-permeable or impermeable.

FIG. 7A shows a device for performing a series of crystallizations within a series of lumens where each lumen comprises a loading 701 and unloading 703 port and a lumen body 702 interconnecting the ports.

FIG. 7B shows a cross section of a device 700 for performing a crystallization within a lumen where the lumen 702 is not enclosed.

FIG. 7C shows a cross section of a device 700 for performing a crystallization within a lumen where the lumens 702 are rectangular in shape.

FIG. 7D shows a cross section of a device 700 for performing a crystallization within a lumen where the lumens 702 are curved or tubular in shape.

FIG. 7E shows a device for performing crystallizations within a series of lumens where the lumens are loaded with samples 705, 707 that are separated by divider or modifier segments 704, 706, 708. It should be appreciated that each discrete sample may have conditions that are potentially unique and unrelated to adjacent samples. The dividers or modifiers positioned between the samples can be permeable, semi-permeable or impermeable.

The series of crystallizations shown in 7E can be created via the same methods used to create samples 4A above. To expedite the process, it is preferable to load some or all of the channels simultaneously.

Figure 8:
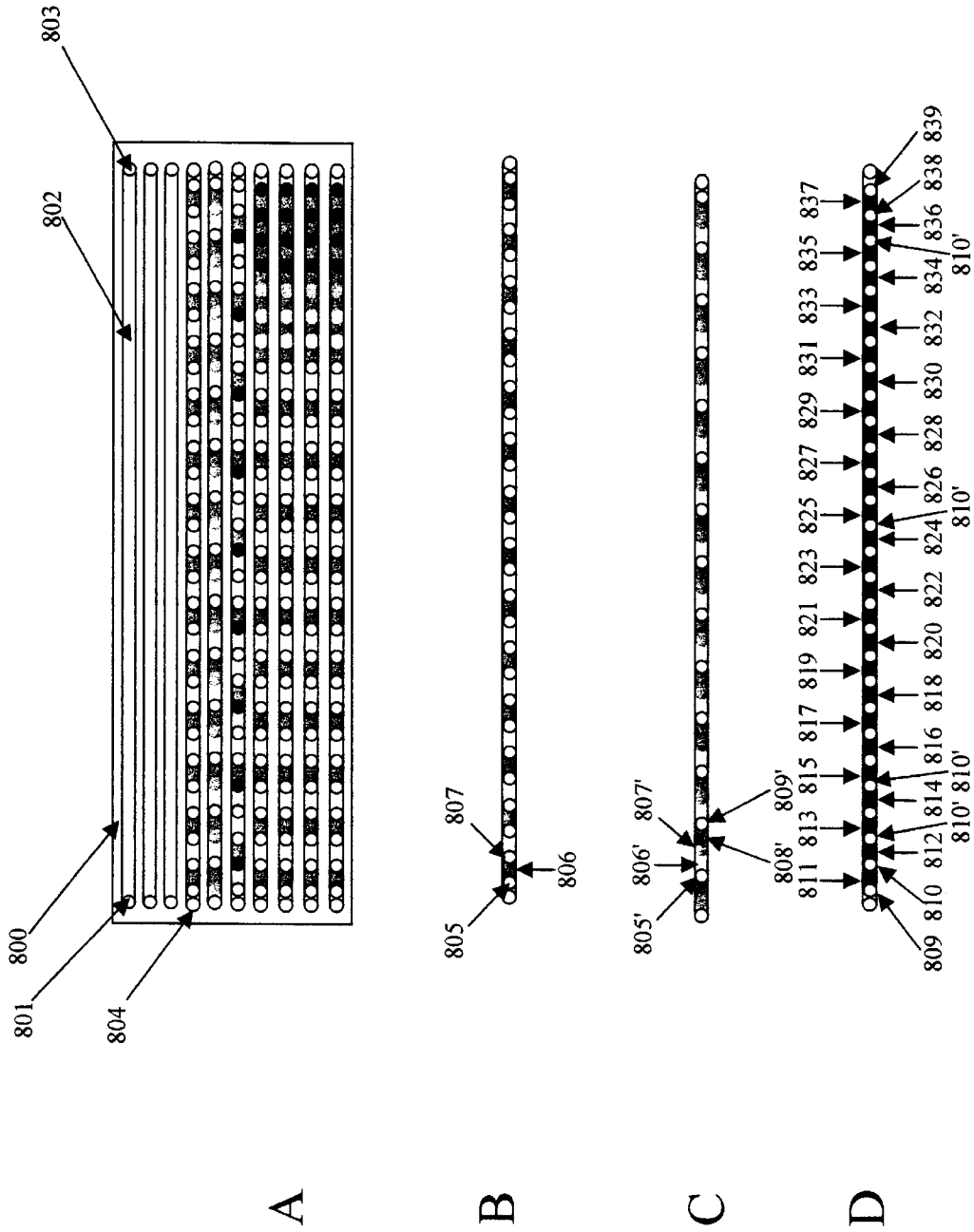
FIG. 8A shows a device for performing a series of different crystallizations within a series of lumens where each lumen comprises a loading and unloading port and a lumen body interconnecting the ports.
FIG. 8B illustrates a single lumen in which a barrier is adjacent to the crystallization condition bounded by second barrier.
FIG. 8C illustrates a lumen comprising a more complex design of crystallizations than the lumen shown in FIG. 8B.
FIG. 8D illustrates a multi-component crystallization being performed in a single lumen.

FIG. 8A shows a device 800 for performing a series of different crystallizations within a series of lumens where each lumen comprises a loading 801 and unloading 803 port and a lumen body 802 interconnecting the ports.

FIG. 8B illustrates a single lumen 802 in which a barrier 805 is adjacent to the crystallization condition 806 bounded by second barrier 807. The crystallization conditions can be a larger volume, or the same volume or smaller volume than the barriers. A more complex form of FIG. 8B, is shown in FIG. 8C.

FIG. 8C illustrates a diffusion crystallization. The barrier 805', which can be either permeable or impermeable, is adjacent to the crystallization condition 806', which is bounded by the barrier 807', which can be either permeable, semi-permeable and is adjacent to crystallization condition 808', which differs from condition 806' in at least one component. Condition 808' is bounded by boundary condition 809', which can be either permeable, semi-permeable or impermeable. Conditions 806' and 808 form a set of linked crystallization conditions, whose rate of equilibration is modulated by the properties of barrier 807'. This example can be easily generalized to an entire crystallization channel or plate by suitable construction of the conditions and the plate itself. This is illustrated with regard to FIG. 8D.

FIG. 8D illustrates a multi-component crystallization being performed in a single lumen. The multi-component crystallization consists of end barriers 809 and 839 and crystallization conditions 811 through 837, each separated from its adjacent neighbor conditions by a permeable or semipermeable barrier 810, repeating along the channel as 810' between each condition 811 through 837. Any number of conditions can be coupled via semipermeable or permeable barriers depending on the dimensions of the lumen, the design of the plate and crystal arrays and the volumes of the various crystal conditions. FIG. 9A shows an embodiment of a device 900 for performing a series of different crystallizations within a series of multi-lumen assemblies 901, 901' where each multi-lumen assembly comprises at least one and preferably two loading 902, 903 and unloading 907, 908 ports and a lumen body 901 interconnecting the ports.

The fluids for each crystallization are contained in two distinct lumens 902, 903, in which fluids from the port are in contact along a shared interface 906. The channels consist of a crystallization condition 909 and a series of crystallization conditions 904 and 904' that are separated by a barrier 905, which may be permeable, semipermeable or impermeable. This arrangement enables the simultaneous examination of many different conditions against a single condition.

FIG. 9B illustrates an enlargement of a lumen of the device shown in FIG. 9A which illustrates some of the different simultaneous diffusions that are made possible by the invention. Crystallization condition 910 is adjacent to permeable or semipermeable barrier 912, which is adjacent to crystallization condition 911. When the intervening barriers are permeable or semipermeable, diffusion occurs through the barrier as shown at 913, where a gradient from condition 910 to condition 911 is occurring through the conditions within 912. Similarly, the diffusion front from 910 into the second channel 916 is shown in 913, and the respective diffusion from 911 into 916 is shown as 914. There is a four-way interface at 915 between 910, 911, 912, and 916. Thus, this method enables the diffusion of crystallization components longitudinally between differing conditions in a manner that can be regulated through the suitable choice of barriers.

The conditions can be examined as part of a time series and the time and location of nucleation, initial crystallization or precipitation can be observed or derived. By using known, or observed diffusion rates, the actual conditions at the nucleation or crystallization points can be determined and used for further, more detailed crystallizations. This method thus allows for a finer and more complete examination of crystallization conditions than can be afforded by single condition mixing of crystallization agents and the material to be crystallized.

The diffusions illustrated here are based on diffusion between first and second adjacent lumens. This method and device design can be extended to multiple adjacent lumens and is illustrated in the triple grouped channels shown in FIG. 10.

Figure 9:
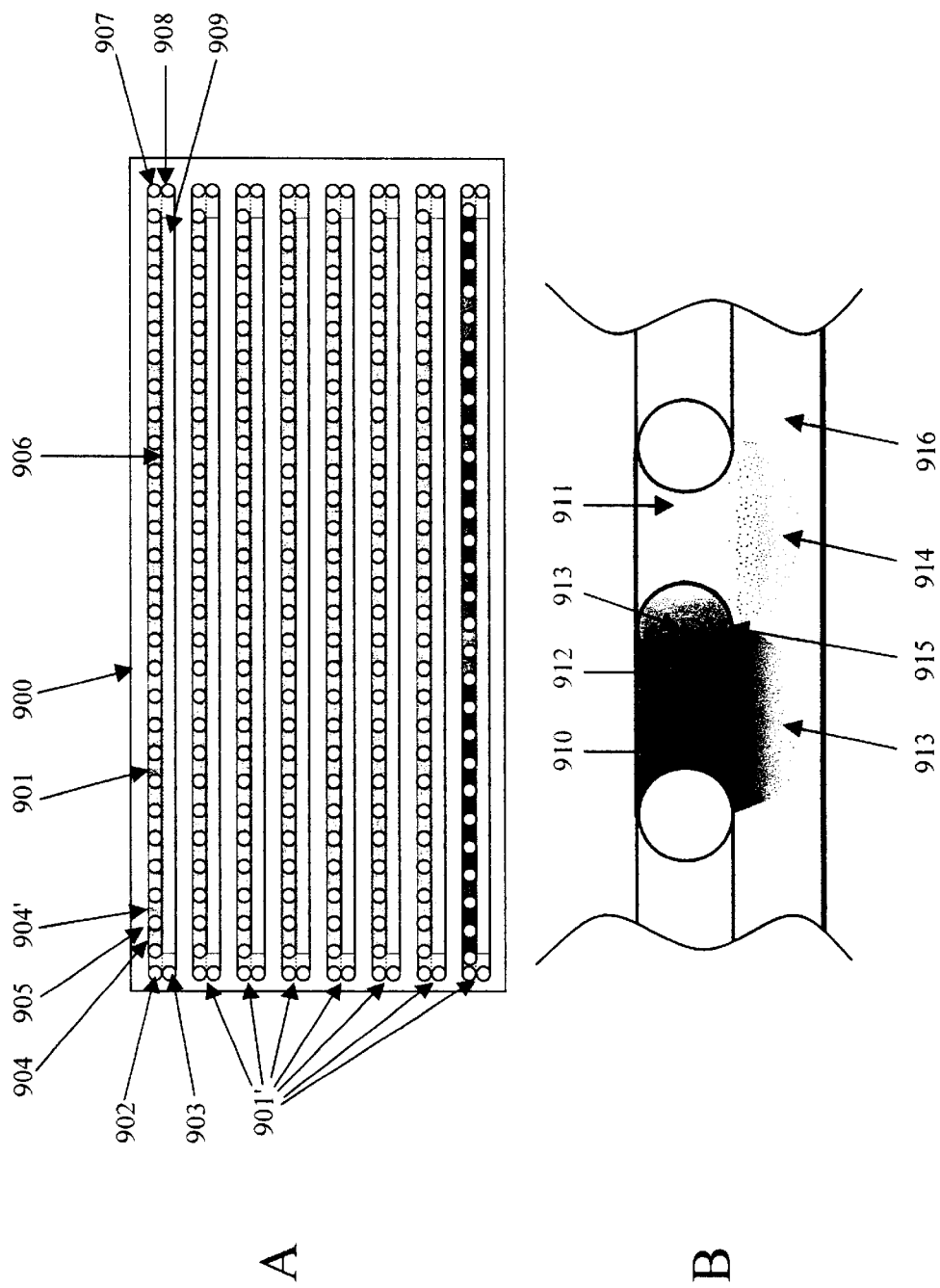
FIG. 9A shows an embodiment of a device for performing a series of different crystallizations within a series of lumens where each lumen comprises a loading and unloading port and a lumen body interconnecting the ports.
FIG. 9B illustrates an enlargement of a lumen of the device shown in FIG. 9A that illustrates some of the different simultaneous diffusions that are enabled by the invention.

While the microlumens shown in FIG. 9 can be either preloaded with a fluid or not, it is preferable that the pairs of lumens 901 be simultaneously loaded via the inlet ports 902 and 903. Having an existing fluid in the microlumen may facilitate maintaining the laminar flow necessary to maintain a uniform interface 906 between the two lumens. A method for loading a single channel has been described above. This process can be used to produce the samples introduced via inlet port 902. Simultaneous with the injection of the material via port 902 is the injection of the desired material 909. This method can be easily generalized to more than two lumens.

Figure 10:
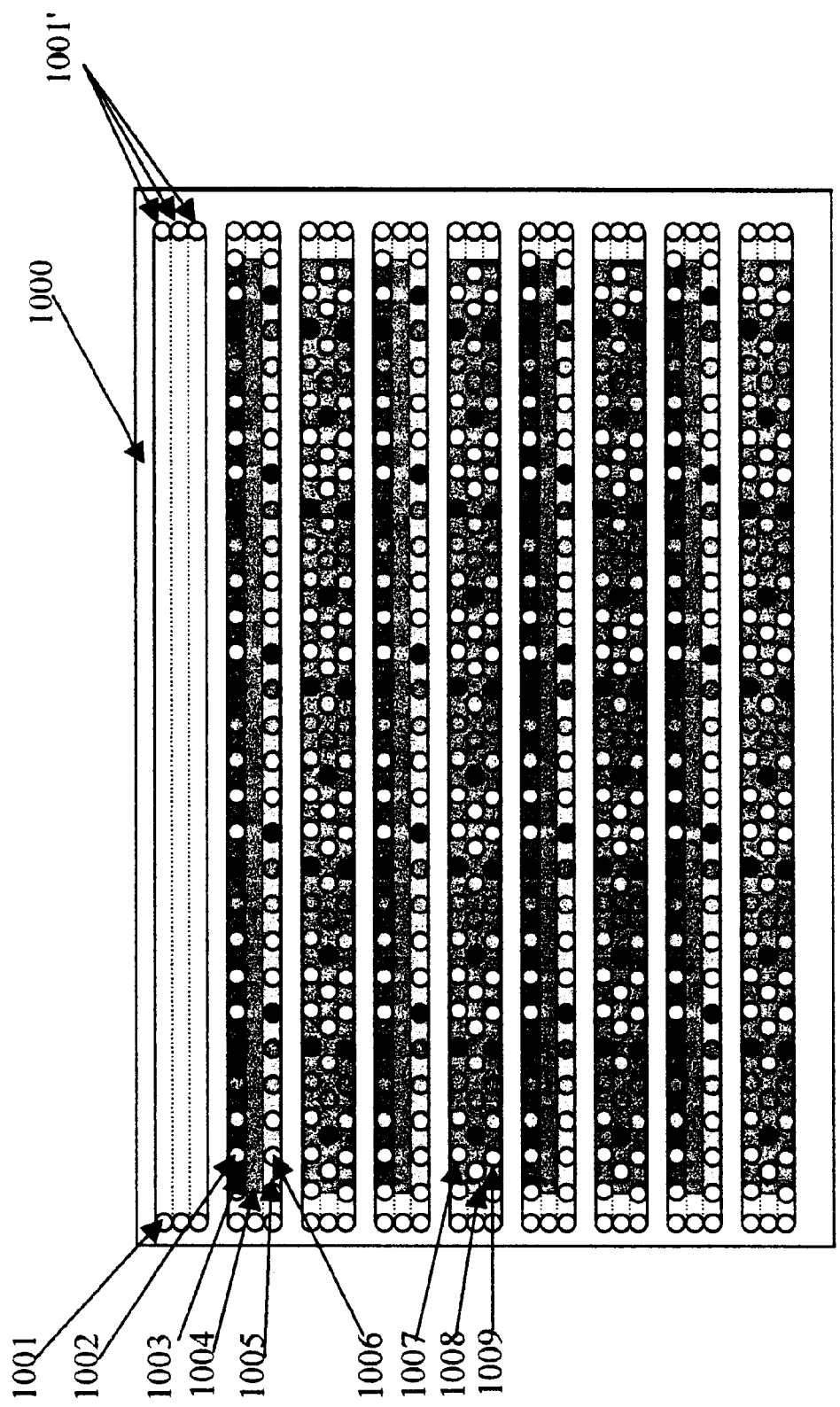
FIG. 10 illustrates a multi-lumen cassette, wherein the crystallization lumens are arranged in groups of three lumens, and have no or limited barriers between common walls.

FIG. 10 illustrates a multi-lumen cassette 1000, wherein the crystallization lumens 1001 are arranged in groups of three lumens, and have no or limited barriers between common walls. Each lumen has at least one inlet or outlet port (1001'). By utilizing triplet channels, simultaneous crystallizations using gradients of materials can be easily performed. The crystallization agents (1002, 1006) can be injected in one or more channels adjacent to a single lumen of the substance to be crystallized (1004). The crystallization agents can have non-permeable or semi-permeable materials separating them, (1003, 1005), or they may be separated by an inert substance, such as a buffer solution. Alternatively, and as a preferred embodiment, the substance to be crystallized (1008) is inserted in all three lumens. In each lumen, crystallization agents(1007,1009) are inserted into the matrix, producing multiple gradients from each crystallization agent. This enables a rapid, multifactorial analysis of the crystallization patterns of the substance to be crystallized. In any given plate (1000) the pattern of crystallization agents can be varied to align substances or to stagger substances or to produce matrices and arrays of substances for crystallization.

Figure 11:
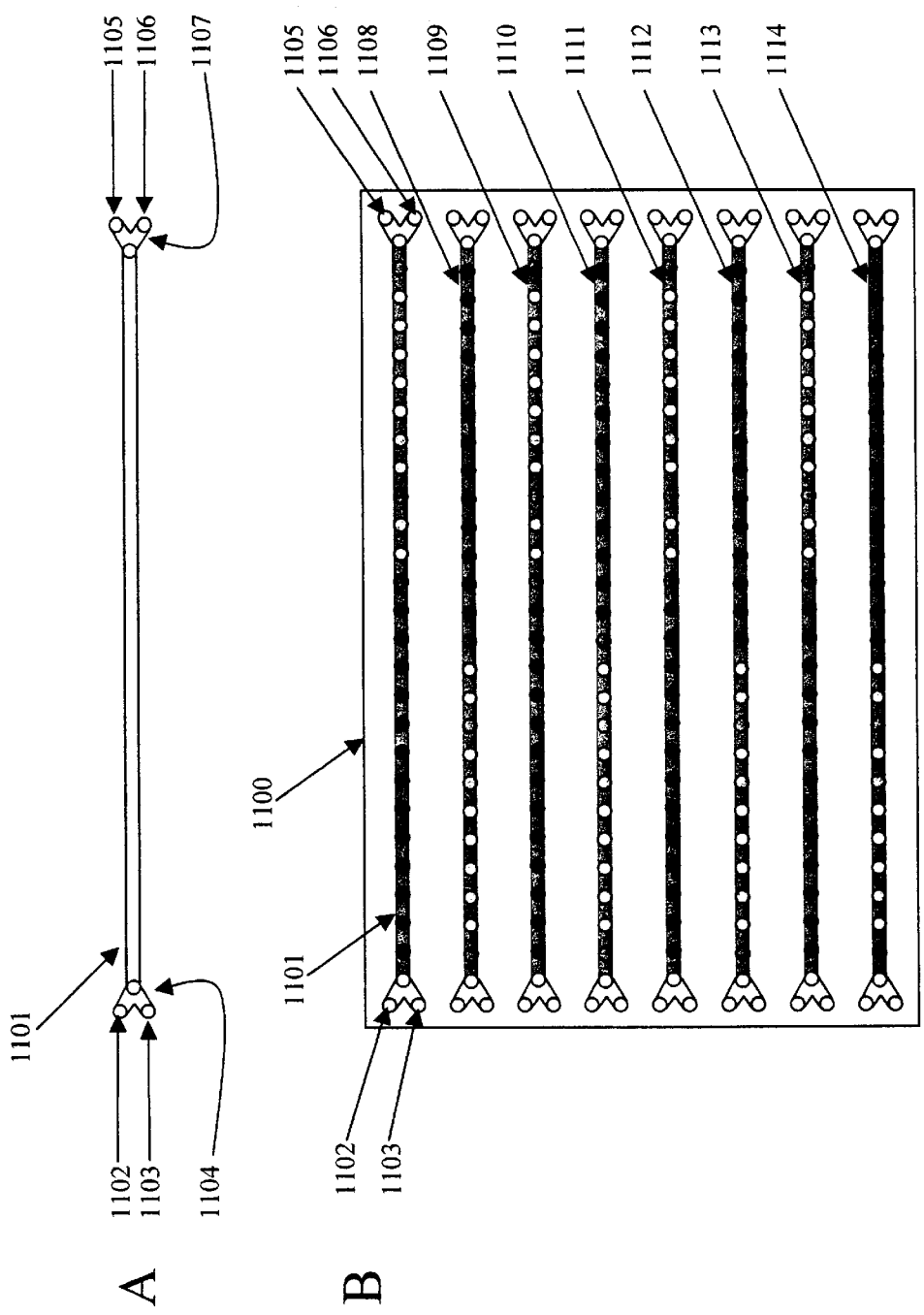
FIG. 11A illustrates a single lumen with integral mixing and harvesting channels.
FIG. 11B shows an embodiment of a device for performing a series of different crystallizations within a series of lumens where each lumen comprises integral mixing and harvesting channels.

FIG. 11A illustrates a single lumen with integral mixing and harvesting channels. The single channel comprises an inlet assembly of at least two inlet ports 1102, 1103 and mixing channel 1104, a crystallization channel 1101 and a harvesting assembly 1107, comprised of at least one harvesting port 105 and preferably two ports 1106 for harvesting.

FIG. 11B shows an embodiment of a device 1100 for performing a series of different crystallizations within a series of lumens 1101, 1108–1114 where each lumen comprises integral mixing and harvesting channels. Conditions with each channel may consist of identical conditions, or of multiple crystallization agents or of multiple substances to be crystallized or any combination thereof.

The "Y" shown in FIGS. 11A and 11B is easily utilized to alternate a series of materials. Syringes or syringe pumps can alternately deliver material to ports 1102 and 1103. Simply, a small interruptible vacuum can be applied to either 1105 or 1106 and the other can be sealed. Alternatively, the vacuum can be applied to both. Whenever a sample is loaded into 1102, port 1103 is sealed and the vacuum is applied at 1105/1106 to transfer the appropriate volume into the "Y" 1104. When the desired volume has been transferred, the pressure differential is removed. Material can then be loaded at 1103, port 1102 is then sealed and a pressure difference sufficient to deliver the required volume into 1104 is applied. The process can then be repeated. For ease of control, it may be preferable to preload the lumens with a hydraulic transfer fluid. Similarly, it is preferable to apply constant pressure difference between the pair 1102/1103 and the pair 1105/1106. The lumen 1101 can then be loaded by alternating the supply of material from 1102 and the supply of material from 1103.

Figure 12:
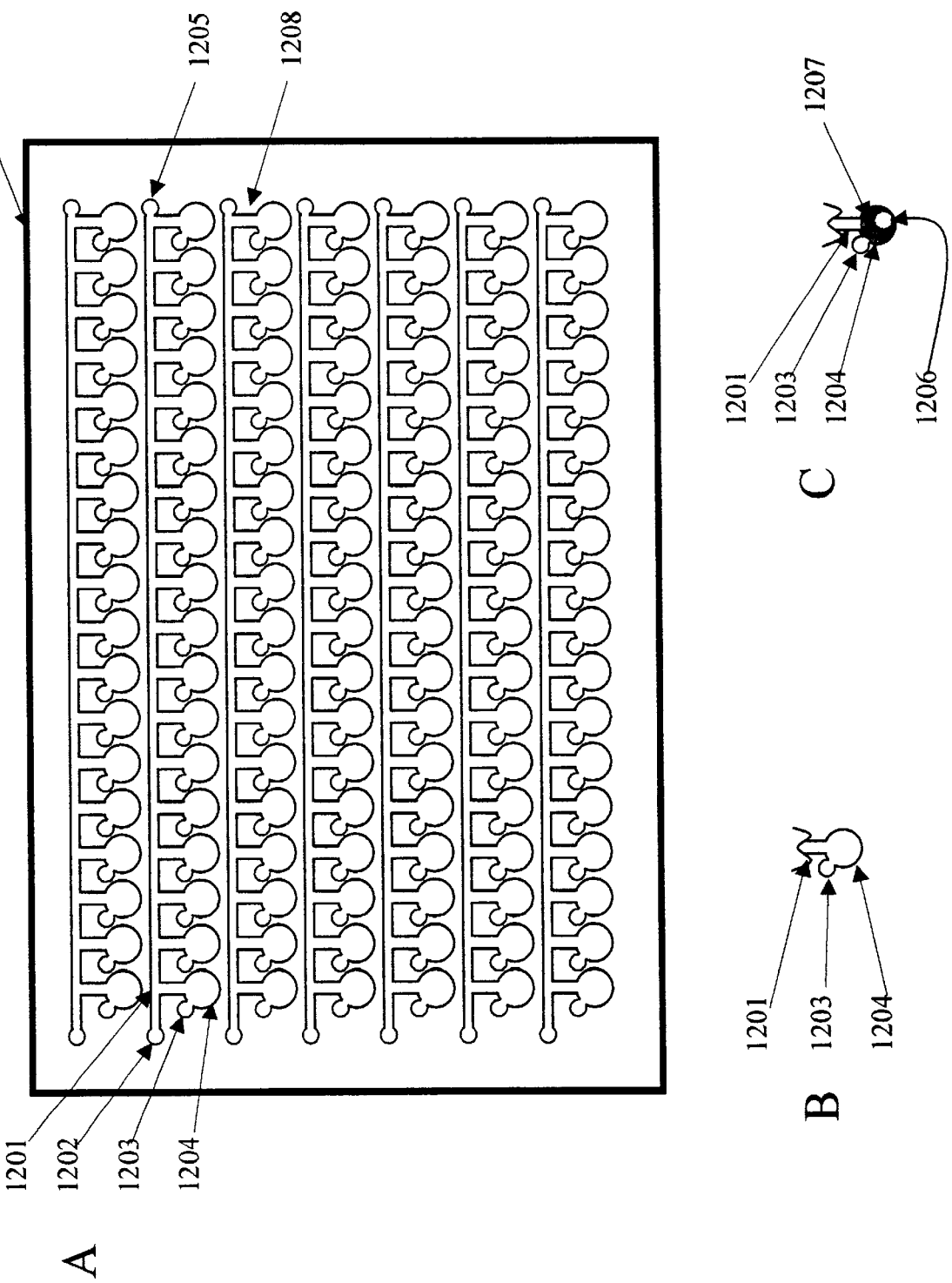
FIG. 12A illustrates a device comprising a series of lumens, each lumen having attached to it an array of individual crystallization cells, each cell having at least one separate inlet or outlet and at least one channel connecting the cell to the lumen.
FIG. 12B illustrates an embodiment of an individual crystallization cell shown in FIG. 12A.
FIG. 12C illustrates an embodiment of an individual crystallization cell shown in FIG. 12A where the cell comprises a crystallization agent and a substance to be crystallized.

FIG. 12A illustrates a device 1200 comprising a series of lumens, each lumen having attached to it an array of individual crystallization cells 1204, each cell having at least one separate inlet 1202 or outlet 1203 and at least one channel connecting the cell to the lumen 1201. Each crystallization cell may have an exclusive inlet and outlet, giving an array of independent cells, or the cells may be linked, or multiplexed with a common inlet or outlet lumen 1201, which can have a single 1202 or multiple ports 1202, 1205. Substances unique to each crystallization cell are loaded via the port 1203, with the excess being drawn off via the common lumen. Substances common to all cells in a sub-array 1208, consisting of port 1202, manifold 1201, port 1205 and all thus linked crystallization cells and ports, can be loaded through ports 1202 and 1205 by any combination of injection of suction via the ports within the sub-array. By suitable application of driving forces, substances can be driven into any one of the attached crystallization cells, either in parallel or individually.

FIG. 12B illustrates an embodiment of an individual crystallization cell shown in FIG. 12A. If the device is to consist of individually accessed crystallization cells, then port 1201 is unique to each cell. If the cassette includes multiple sub-arrays, then lumen 1201 may be common with the other crystallization cells of the sub-array.

FIG. 12C illustrates an embodiment of an individual crystallization cell 1204 shown in FIG. 12A where the cell comprises a crystallization agent 1207 and a substance 1206 to be crystallized. The exact nature of the meniscus between the substances is highly dependent upon both the sequence of addition of the crystallization materials, their relative volume and the surface properties of the supporting materials of the cassette, e.g. surface energy, hydrophobicity, hydrophilicity, or adsorbed materials.

4. Delivery of Materials to Microsized Lumens

Materials may be added to the devices of the present invention by a variety of different methods and mechanisms. For example, material may be added to a given lumen by the sequential addition of the volumes of materials that need to be added or may be delivered as a single bolus. Commercial robots such as the Staubli can deliver small volumes of material with the high degree of accuracy needed to repeatedly deliver the necessary drops into entry ports of the lumens. For improved accuracy, multiple deliveries can be used to create the final, larger volume, from a series of smaller volumes.

Volume of materials can be delivered by a number of different mechanisms, such as ultrasonic dispensers, peristaltic pumps, syringes, syringe pumps or stepper motor driven plungers. Materials can be delivered to multiple different lumens individually, in parallel within a channel, or in parallel across the entire device. For some embodiments, it may be desirable to deliver two or three conditions simultaneously for optimal loading. Alternatively, it is possible to use pin arrays to deliver the fluid.

The device may also be docked with a manifold in order to deliver materials to the lumens of the device. This manifold can be mated with at least one or multiple inlet ports. The channels in the chip can then be filled individually, or in parallel from the manifold. The filling cycle may be entirely in parallel, or the filling cycle may involve multiple docking events. If the device is docked multiple times to different manifolds, the materials can be added by alternately mating the device with, for example, a protein manifold, a barrier manifold, and a crystallization manifold. The materials may be pressure driven into the device, or may be applied with vacuum, or a combination thereof. Under some constructs, it may be advantageous to pre-fill the device with a fluid. This fluid can then be displaced by the pressure addition of material, or this fluid may be removed actively be an applied vacuum, or a combination thereof to deliver the necessary fluids. Pre-filling the device has advantages in the fluidics, and also for the alteration or modulation of the surface properties of the lumen.

5. Microlumen Filling using Centrifugal Force

One feature of the present invention is the use of centrifugal force to cause material to flow within the microlumens of devices according to the present invention. Through the use of centrifugal force, fluids can be loaded, measured, filtered, mixed and incubated within a lumen. The centrifugal force serves to generate hydrostatic pressure to drive the fluids through the lumens, reservoirs, filters and manifolds. This method has the advantages of speed, tightly enclosed fluids to minimize evaporation, and simplicity since there are no moving parts on the device to break or become fouled through the application of external energies. The use of centrifugal force is compatible with a wide variety of fluids.

A particular advantage of the use of centrifugal force is the ability to make hundreds to thousands to hundreds of thousands of replicate volume measurements simultaneously. In addition, since a common amount of force can be applied to each lumen, the replicate volume measurements can also be made with a high degree of reproducibility.

A further feature of the use of a device employing centrifugal force is the ability to preload crystallization agents. This can be used to dramatically enhance the speed and efficiency of the crystallization setup.

Figure 13:
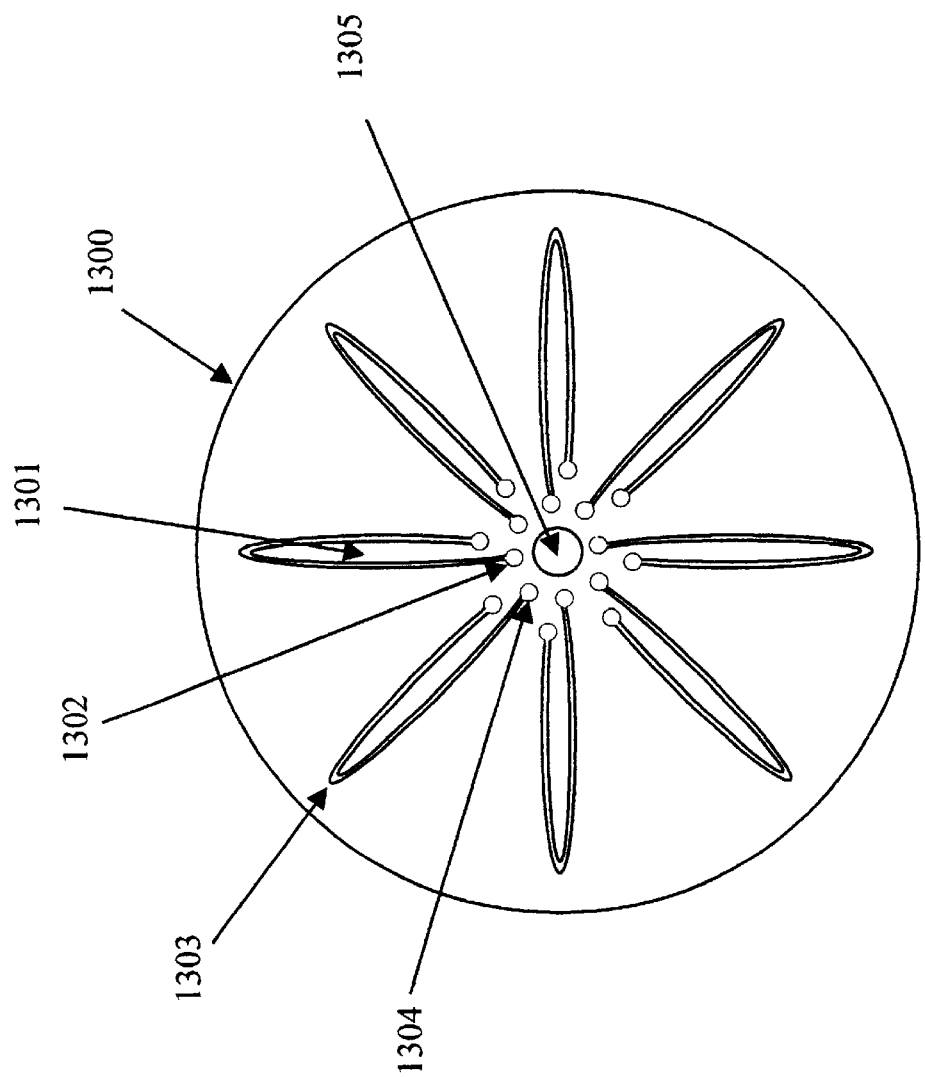
FIG. 13 illustrates a device for forming crystallizations by rotation of the device.

FIG. 13 illustrates a device for forming crystallizations by rotation of the device, thereby applying centrifugal force. The device 1300 comprises multiple crystallization wells 1301, each having at least one inlet port 1302, a crystallization channel 1303 and an outlet port 1304. It is understood that during centrifugation, the radially outermost port will, due to centrifugal forces be the outlet port. However, for the purposes of loading the cassette, either port 1302, 1304 may be used as an inlet or outlet port. The device can have a centering device 1305 to center the device during centrifugation, or alternatively, the device may be inserted in a receiver designed to mate with the device.

As can be seen, the device is similar in design to a compact disc, comprising a flat, circular plate of substrate with a hole in the middle, preferably at the center of mass of the device. Incorporated into the substrate is an array of crystallization chambers. This design allows the crystallization agents to be added to the device. Then, when the device is rotated, the crystallization agents in the different chambers are each caused to enter a corresponding crystallization well.

Given the symmetry of the design and the uniformity of the centrifugal force that is applied, the design of the device provides for a compact system where crystallization agents can be first added and stored in the device. Then, when the device is ready to be used, the device can be rotated to cause the prior added crystallization agents to move within the device. The design of the device also allows for multiple devices to be stacked upon each other. This allows for a great number of devices to be processed in parallel.

FIG. 14 illustrates another embodiment of a device 1400 that is designed to move fluids within the device by centrifugal force. This design allows for the precise measurement of very small volumes without the use of moving parts, electromotive force or active pumps within the device. The device consists of at least two inlet chambers 1401, 1401', a measurement channel 1402 for each inlet, a waste channel 1403 from each inlet 1401 to a waste reservoir 1404 or outlet, a mixing manifold 1405 connecting the measurement channels 1402, 1402' and the crystallization chamber 1406. The manifold, can encompass the inlet port, or by pass it. The measurement channels can be of identical or differing volumes, dependent upon the need. The crystallization chamber can be of any shape, shown here as either circular 1406 or rectangular 1406'. Only one waste channel is illustrated, but each measurement channel has an associated waste channel. These channels can be independent, or by suitable design can form a manifold.

The device may be employed as follows; into each inlet chamber 1401, a volume of crystallization agent or substance to be crystallized is added. The volume that is added does not need to be precise or accurate. Instead, it is sufficient that the volume is greater than a minimum volume for the measurement channel 1402. The crystallization agents can be dispensed in advance of the substance to be crystallized, enabling the device to be made in advance and used as needed. Once the inlet chambers are all filled, the device is centrifuged with the centrifugal force vector approximately aligned as shown, for the loading spin (A). The centrifugal force fills the measurement channel 1402 completely, leaving some residue in the inlet chamber 1401. A subsequent measurement spin (B), removes the excess from the inlet chamber and deposits the excess in the waste reservoir 1404 or port, leaving the inlet chamber empty. At this point, the device may be stored until needed. The inlet ports may be sealed by the application of a tape, lid, septum, or by stacking the devices together.

The substance to be crystallized is then added into each inlet chamber 1401'. The volume does not need to be precise or accurate. Instead, it is sufficient that the volume be greater than a certain minimum for the measurement channel 1402'. Once the inlet chambers are all filled, the device is centrifuged with the centrifugal force vector as shown, for the loading spin (A). This fills the measurement channel 1402' completely, leaving some residue in the inlet chamber 1401'. A subsequent measurement spin (B) with the centrifugal force vector approximately in this direction, removes the excess from the inlet chamber and deposits the excess in the waste reservoir 1404 or port, leaving the inlet chamber empty. At this point, the device may again be stored until needed. The inlet ports may be sealed by the application of a tape, lid, septum, or by stacking the plates together.

Crystallization, or the test of crystallization is initiated by centrifugation with the centrifugal force vector approximately in the direction of the crystallization initiation spin (C). This drives the crystallization agent or agents and the substance to be crystallized through a mixing manifold 1405 into a crystallization chamber 1406.

FIGS. 15A–15G illustrate an embodiment of a crystallization device driven by centrifugal force. It is noted that different sets and subsets of combinations described herein can be performed without departing from the present invention.

Figure 15A:
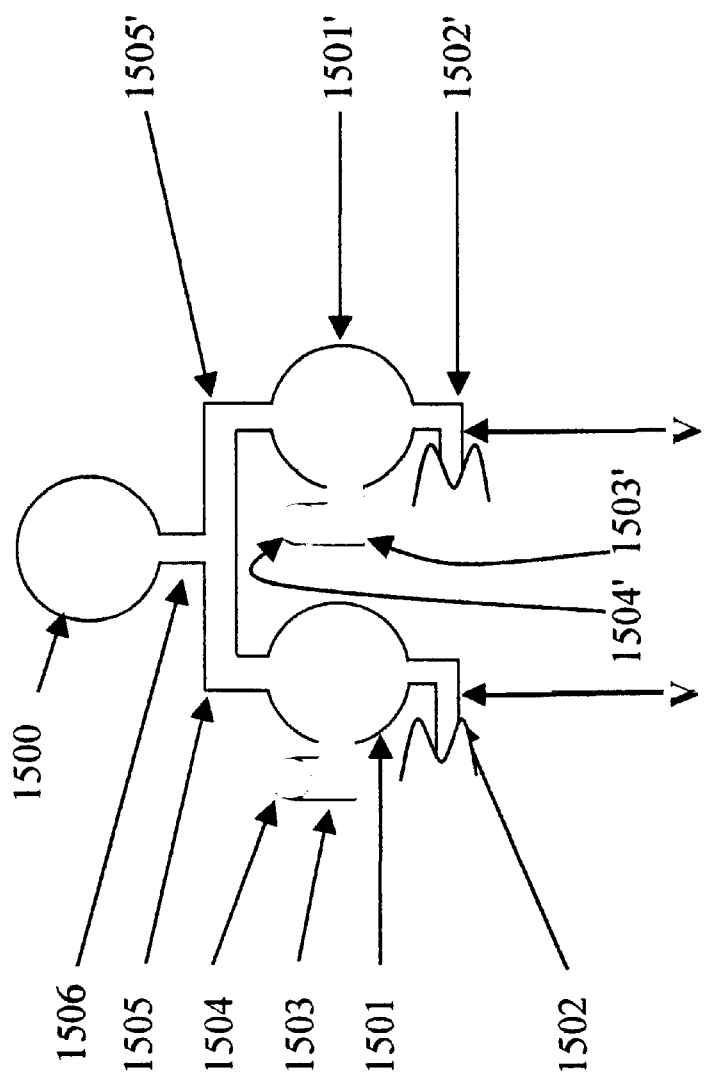
FIGS. 15A–15G illustrate an embodiment of a centrifugally driven crystallization device.

FIG. 15A illustrates a repeating unit of the centrifugal array in more detail. Here an embodiment of one inlet for crystallization agents 1501 and one inlet for a substance to be crystallized 1501' is shown. Note that the lumens 1502, 1502' connecting to the measurement lumens have a short neck near the inlet chamber, orthogonal to the measurement spin, V represents the measured volume after the measurement spin. During the measurement spin, excess material in the inlet chamber, and the excess above V is centrifugally ejected through lumens 1503, 1503' and thence through lumens 1504, 1504' to the exit port or reservoir. Note that lumens 1503, 1503', also have a narrow neck, initially oriented parallel to and in the opposite direction to the loading spin vector, ensuring that the liquids proceed down 1502 or 1502' to the measurement lumens.

Figure 15B:
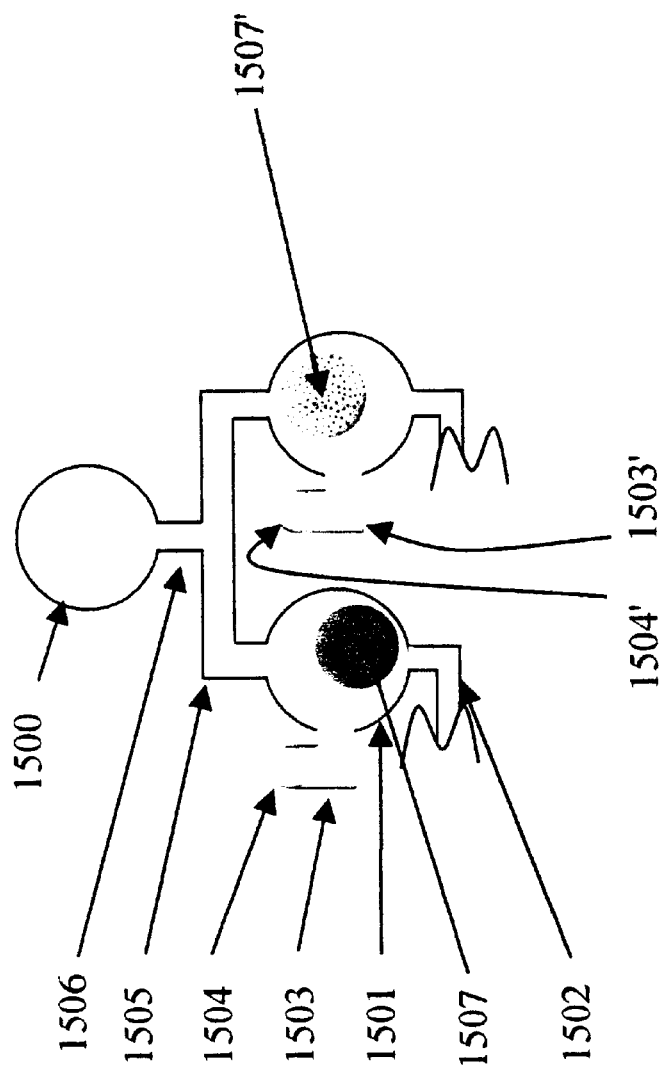

FIG. 15B shows the process of using a device that utilizes centrifugal energy. Here a crystallization agent 1507 has been added into the entry port, or well 1501. Also shown is the material to be crystallized 1507' in a second entry port or well. These materials need not be added contemporaneously.

Figure 15C:
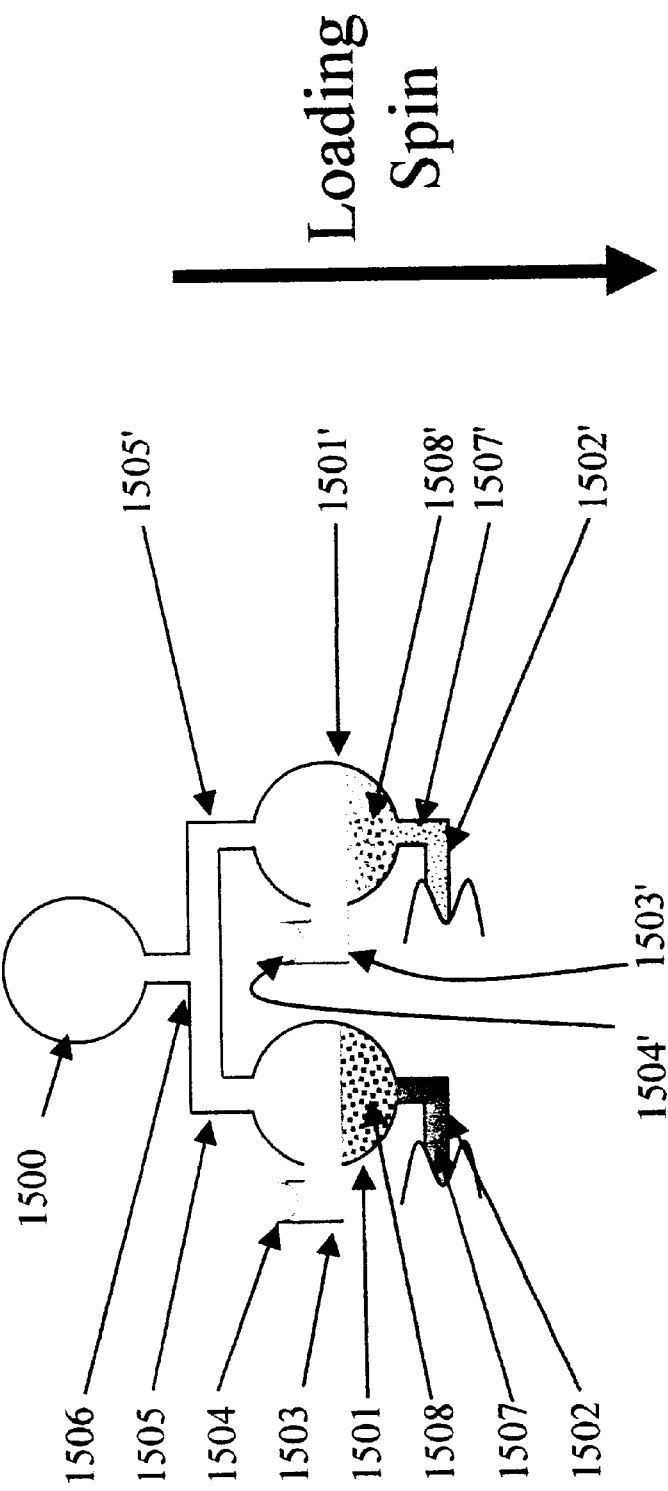

FIG. 15C illustrates the effect of centrifugal force on the samples that were loaded in FIG. 15B. Here, the bulk of the material 1507 and 1507' has proceeded to fill the respective measurement lumens 1502 and 1502'. This leaves some amount of excess material 1508 and 1508' in the initial loading wells 1501 and 1501', respectively.

Figure 15D:
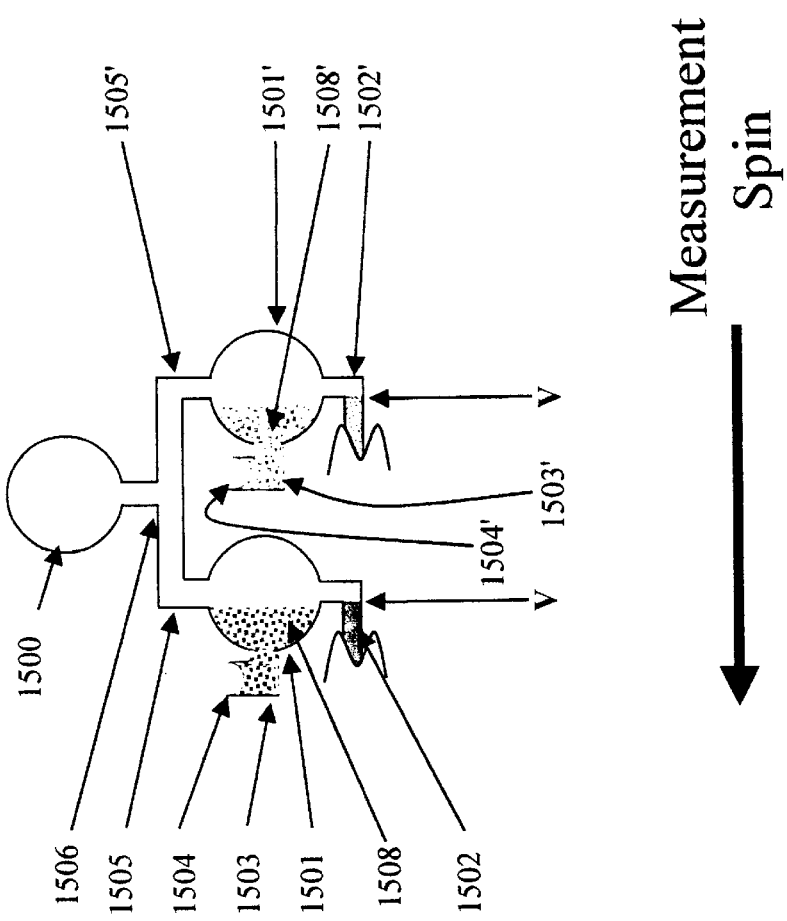

In FIG. 15D, the centrifugal force vector has been changed such that the force now directs the excess crystallization agent and excess material to be crystallized 1508 and 1508' toward the waste ports 1504, 1504' via the respective waste lumens 1503, 1503'. The result is to leave the measurement channel filled with material to the point V in every measurement lumen.

Figure 15E:
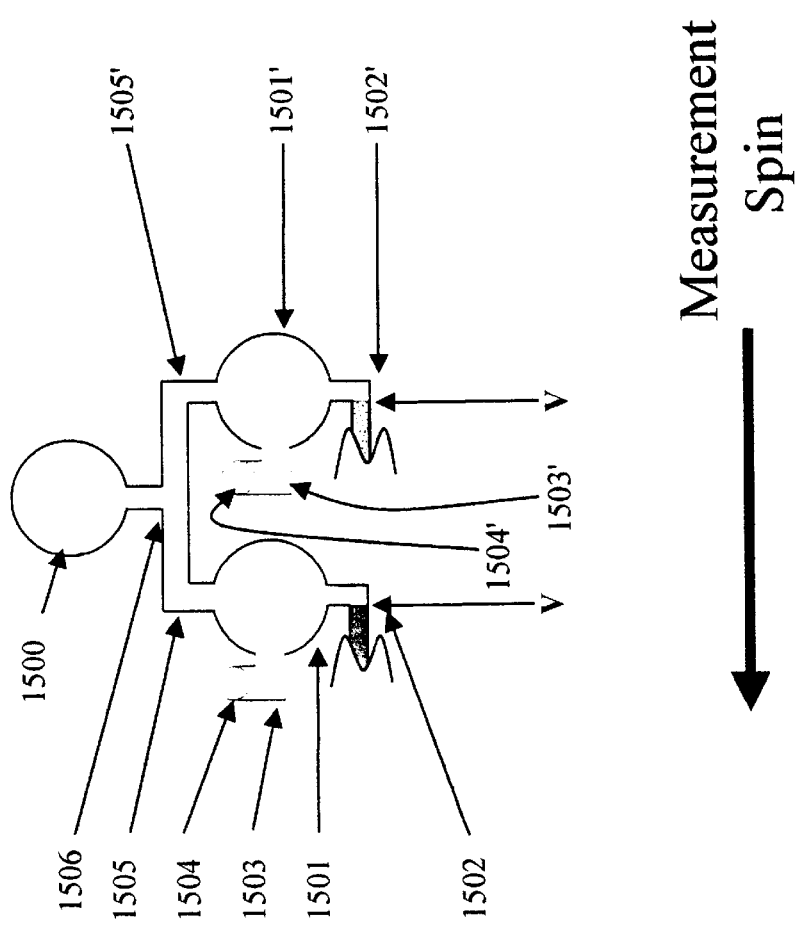

FIG. 15E shows the final result, with each lumen filled to point V, resulting in precise volume measurements.

Figure 15F:
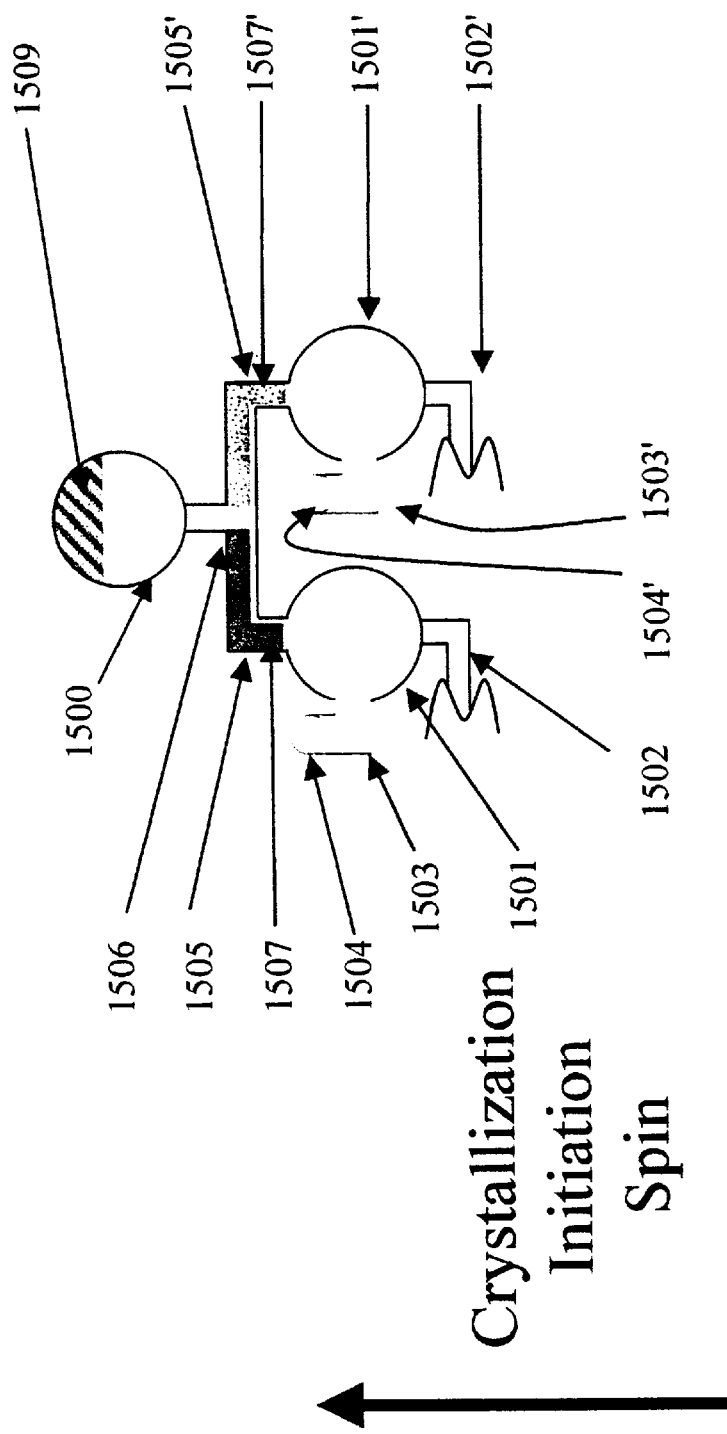

In FIG. 15F, the centrifugal force vector has been altered again to align in the direction shown. This drives the crystallization agent 1507 and the material to be crystallized 1507' from the measurement lumens 1502, 1502', across the inlet ports 1501, 1501' and through a manifold 1505, 1505' to the mixing manifold 1506 and thence into the crystallization chamber 1500, as the mixed material 1509.

Figure 15G:
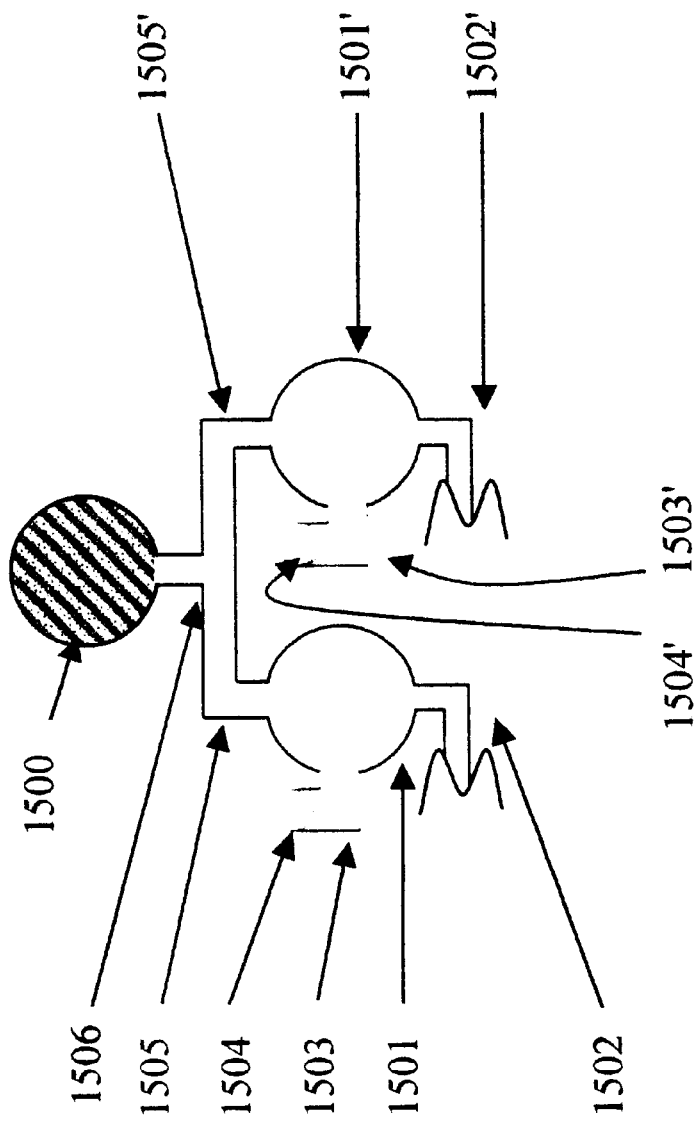

FIG. 15G shows the final result, with the crystallization chamber 1500 filled with the combination of the material to be crystallized and the crystallization agent, or agents.

6. Use of the Devices of the Present Invention to Determine Crystal Growth Conditions One of the intended uses of the devices of the present invention is for improving the process of discovering novel crystal growth conditions. By using the devices of the present invention, a simultaneous, multiple factor approach can be implemented.

Current methods of vapor diffusion, hanging drop, sitting drop and dialysis evaluate a single test condition in each instance. By contrast, the present invention allows for multiple different crystallization conditions to be created in the same lumen, thereby allowing for multiple different crystallization conditions to be tested. In some embodiments, gradients are created which create the multiple different crystallization conditions. Diffusion of either the sample being evaluated and/or the enclosing medium having a viscosity such that the diffusion of the chemical moieties for crystallization is much faster than the diffusion of bulk material allows for the gradients to be created. This can be achieved either through intrinsically viscous materials or additives such as agarose, acrylamide, silica gel, or PEG, or by the use of filter plugs, or by the use of enclosing channels that are sufficiently thin in at least one dimension to limit macroscopic flow such that diffusion of the chemical moieties for crystallization dominate. These samples can be affected by sample droplets in a channel, droplets within an enclosing crystallization medium, or crystallization droplets or islands within an enclosing volume of sample.

While the present invention is disclosed with reference to preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims. The patents, papers, and books cited in this application are to be incorporated herein in their entirety.

We claim:

1. A method for determining crystallization conditions for a protein, the method comprising:
    within a microfluidic device, delivering material to an enclosed microvolume via one or more lumens that each have a cross sectional diameter of less than 500 microns to form a plurality of different crystallization samples within the enclosed microvolume, the plurality of different crystallization samples comprising a protein to be crystallized and crystallization conditions which vary among the plurality of different crystallization samples;
    allowing crystals of the protein to form in the plurality of crystallization samples within the microfluidic device; and
    identifying which of the plurality of crystallization samples within the microfluidic device comprise a precipitate or a crystal of the protein.

2. A method according to claim 1 wherein the en closed microvolume is a lumen.

3. A method according to claim 1 wherein the enclosed microvolume is a lumen with a cross sectional diameter of less than 2.5 mm.

4. A method according to claim 1 wherein the enclosed microvolume is a lumen with a cross sectional diameter of less than 1 mm.

5. A method according to claim 1 wherein the enclosed microvolume is a lumen with a cross sectional diameter of less than 500 microns.

6. A method according to claim 1 wherein the enclosed microvolume is a microchamber.

7. A method according to claim 1 wherein the enclosed microvolume is at least partially enclosed within a substrate which comprises other enclosed microvolumes which also comprise crystallization samples.

8. A method according to claim 1 wherein the enclosed microvolume is at least partially enclosed within a card shaped substrate.

9. A method according to claim 1, the method further comprising performing a spectroscopic analysis on a precipitate or crystal formed within the microvolume.

10. A method according to claim 9, wherein the spectroscopic analysis is selected from the group consisting of Raman, UV/VIS, IR, and x-ray spectroscopy.

11. A method according to claim 9, wherein the spectroscopic analysis is x-ray spectroscopy.

12. A method according to claim 11, wherein x-ray spectroscopy is performed such that a portion of the microvolume that the x-ray beam traverses contains at least as many electrons as is contained in a material defining the portion of the microvolume that the x-ray beam traverses.

13. A method according to claim 11, wherein x-ray spectroscopy is performed such that a portion of the microvolume that the x-ray beam traverses contains at least three times as many electrons as is contained in a material defining the portion of the microvolume that the x-ray beam traverses.

14. A method according to claim 11, wherein x-ray spectroscopy is performed such that a portion of the microvolume that the x-ray beam traverses contains at least five times as many electrons as is contained in a material defining the portion of the microvolume that the x-ray beam traverses.

15. A method according to claim 11, wherein x-ray spectroscopy is performed such that a portion of the microvolume that the x-ray beam traverses contains at least ten times as many electrons as is contained in a material defining the portion of the microvolume that the x-ray beam traverses.

16. A method according to claim 1, wherein material defining the microvolume defines a groove that reduces a number of electrons that an x-ray beam used to perform x-ray spectroscopy of a crystal within the microvolume traverses in the process of performing x-ray spectroscopy on the sample within the microvolume.

17. A method according to claim 1, wherein the method further comprises forming the plurality of different crystallization samples within the enclosed microvolume.

18. A method according to claim 1, wherein one or more dividers are positioned within the enclosed microvolume to separate adjacent crystallization samples within the enclosed microvolume.

19. A method according to claim 18, wherein the one or more dividers are formed of an impermeable material.

20. A method according to claim 18, wherein the impermeable material is an impermeable liquid.

21. A method according to claim 18, wherein the impermeable material is an impermeable solid.

22. A method according to claim 18, wherein the one or more dividers are formed of a permeable material.

23. A method according to claim 18, wherein the one or more dividers are formed of a semipermeable material.

24. A method according to claim 23, wherein the semipermeable material is a gas.

25. A method according to claim 23, wherein the semipermeable material is a liquid.

26. A method according to claim 23, wherein the semipermeable material is a gel.

27. A method according to claim 18, wherein at least one of the one or more dividers form an interface selected from the group consisting of liquid/liquid, liquid/gas interface, liquid/solid and liquid/sol-gel interface.

28. A method according to claim 18, wherein the one or more dividers are selected from the group consisting of a membrane, gel, frit, and matrix.

29. A method according to claim 18, wherein the one or more dividers function to modulate diffusion characteristics between adjacent crystallization samples.

30. A method according to claim 18, wherein at least one of the one or more dividers is formed of a semipermeable material which allows diffusion between adjacent crystallization samples.

31. A method for determining crystallization conditions for a protein, the method comprising:

within a microfluidic device, delivering material to a plurality of enclosed microvolumes via one or more lumens that each have a cross sectional diameter of less than 500 microns to form a plurality of different crystallization samples within the plurality of enclosed microvolumes, each microvolume comprising two or more crystallization samples, the different crystallization samples comprising a protein to be crystallized and crystallization conditions which vary among the plurality of different crystallization samples;

allowing crystals of the protein to form in the plurality of crystallization samples; and identifying which of the plurality of crystallization samples comprise a precipitate or a crystal of the protein.

32. A method according to claim 11, wherein the x-ray spectroscopy is x-ray diffraction.

33. A method according to claim 11, wherein x-ray spectroscopy is performed such that a portion of the crystal or precipitate that the x-ray beam traverses contains at least as many electrons as is otherwise traversed by the x-ray beam when traversing a device comprising the microvolume.

34. A method according to claim 11, wherein x-ray spectroscopy is performed such that a portion of the crystal or precipitate that the x-ray beam traverses contains at least three times as many electrons as is otherwise traversed by the x-ray beam when traversing a device comprising the microvolume.

35. A method according to claim 11, wherein x-ray spectroscopy is performed such that a portion of the crystal or precipitate that the x-ray beam traverses contains at least five times as many electrons as is otherwise traversed by the x-ray beam when traversing a device comprising the microvolume.

36. A method according to claim 11, wherein x-ray spectroscopy is performed such that a portion of the crystal or precipitate that the x-ray beam traverses contains at least ten times as many electrons as is otherwise traversed by the x-ray beam when traversing a device comprising the microvolume.

37. A method according to claim 31, wherein each microvolume comprising a plurality of crystallization samples.

38. A method according to claim 11, wherein x-ray spectroscopy is performed such that a portion of the microvolume that the x-ray beam traverses contains at least half as many electrons as is contained in a material defining the portion of the microvolume that the x-ray beam traverses.

* * * * *

(12) EX PARTE REEXAMINATION CERTIFICATE (6738th)
United States Patent
David et al.

(10) Number: US 6,719,840 C1
(45) Certificate Issued: Mar. 31, 2009

(54) IN SITU CRYSTAL GROWTH AND CRYSTALLIZATION

(75) Inventors: Peter R. David, Palo Alto, CA (US); Nathaniel E. David, San Diego, CA (US)

(73) Assignee: Takeda San Diego, Inc., San Diego, CA (US)

Reexamination Request:
No. 90/008,268, Oct. 10, 2006

Reexamination Certificate for:
Patent No.: 6,719,840
Issued: Apr. 13, 2004
Appl. No.: 09/877,405
Filed: Jun. 8, 2001

(51) Int. Cl.
*C30B 7/00* (2006.01)
*G01N 25/00* (2006.01)
*G01N 25/14* (2006.01)

(52) U.S. Cl. .................. 422/245.1; 117/68; 117/200; 117/206; 117/69; 117/900

(58) Field of Classification Search .................. None
See application file for complete search history.

(56) References Cited

U.S. PATENT DOCUMENTS

| | | | |
|---|---|---|---|
| 6,258,331 | B1 | 7/2001 | Sanjoh |
| 6,296,673 | B1 | 10/2001 | Santarsiero et al. |
| 6,409,832 | B2 | 6/2002 | Weigl et al. |
| 6,719,840 | B2 | 4/2004 | David et al. |
| 6,818,395 | B1 | 11/2004 | Quake et al. |
| 6,899,137 | B2 | 5/2005 | Unger et al. |
| 6,911,345 | B2 | 6/2005 | Quake et al. |

OTHER PUBLICATIONS

U.S. Appl. No. 60/186,856, Marc Unger.
Chayen, et al., "Trends and Challenges in Experimental Macromolecular Crystallography," Quarterly Reviews of Biophysics, 29, 3, pp. 227–278 (1996).
Salemme, F.R., "A Free Interface Diffusion Technique for the Crystallization of Proteins for X–Ray Crystallography," Archives of Biochemistry and Biophysics, 151, pp. 533–539 (1972).
Yokohama, et al., "Crystal Growth Rates of Tricaprin and Trilaurin Under High Pressures," Journal of Crystal Growth, 191, pp. 827–833 (1998).
Deposition of Steven T. Wereley, Ph.D. Provided in regard to Patent Interference No. 105,403., (*Bernard Santarsiero, Raymond C. Stevens, Peter G. Schultz, Joseph M. Jaklevic, Derek T. Yegian, Earl Cornell, Robert A. Nordmeyer, Jian Jin, William F. Kolbe, Arthur L. Jones, Donald C. Uber—Junior Party*, (Patents 6,296,673, 6,630,006, 6,911,056, 6,932,845, and 6,951,575) v. *Lawrence James Delucas—Senior Party*, (U.S. Appl. No. 10/160,572), (pp. 1–106), (New York, New York; Jul. 11, 2006).
Deposition of Ian Andrew Wilson Provided in regard to Patent Interference No. 105,403., (*Bernard Santarsiero, Raymond C. Stevens, Peter G. Schultz, Joseph M. Jaklevic, Derek T. Yegian, Earl Cornell, Robert A. Nordmeyer, Jian Jin, William F. Kolbe, Arthur L. Jones, Donald C. Uber—Junior Party*, (Patents 6,296,673, 6,630,006, 6,911,056, 6,932,845, and 6,951,575) v. *Lawrence James Delucas—Senior Party*, (U.S. Appl. No. 10/160,572), (pp. 1–78), (San Diego, California; Jun. 22, 2006).

*Primary Examiner*—Krisanne Jastrzab

(57) ABSTRACT

A method is provided for determining crystallization conditions for a material, the method comprising: taking a plurality of different crystallization samples in an enclosed microvolume, the plurality of crystallization samples comprising a material to be crystallized and crystallization conditions which vary among the plurality of crystallization samples; allowing crystals of the material to form in plurality of crystallization samples; and identifying which of the plurality of crystallization samples form crystals.

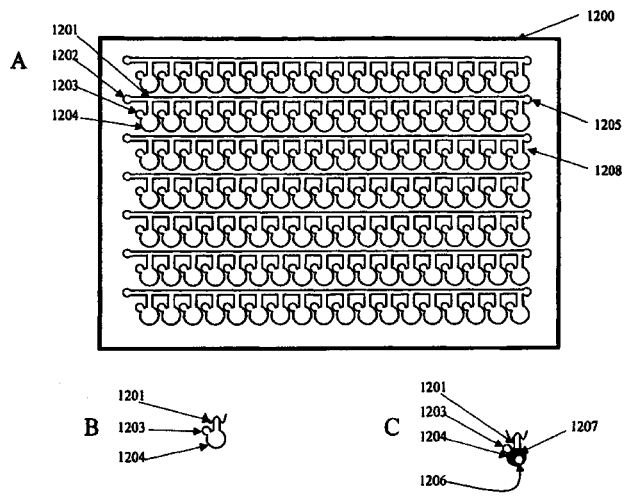

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 18, 31 and 37 are cancelled.

Claims 1, 9, 16, 19–23, 27–30, 33–36 and 38 are determined to be patentable as amended.

Claims 2–8, 10–15, 17, 24–26 and 32, dependent on an amended claim, are determined to be patentable.

1. A method for determining crystallization conditions for a protein, the method comprising:
    within a microfluidic device, delivering material to an enclosed microvolume via one or more lumens that each have a cross sectional diameter of less than 500 microns to form a plurality of different crystallization samples within the enclosed microvolume *wherein the plurality of different crystallization samples are separated from each other within the enclosed microvolume by one or more dividers positioned within the enclosed microvolume*, the plurality of different crystallization samples comprising a protein to be crystallized and crystallization conditions which vary among the plurality of different crystallization samples;
    allowing crystals of the protein to form in the plurality of crystallization samples within the microfluidic device; and
    identifying which of the plurality of crystallization samples within the microfluidic device comprise a precipitate or a crystal of the protein.

9. A method according to claim 1, the method further comprising performing a spectroscopic analysis on a precipitate or crystal [formed] within the microvolume.

16. A method according to claim [1] *33*, wherein material defining the microvolume defines a groove that reduces a number of electrons that an x-ray beam used to perform x-ray spectroscopy of a crystal within the microvolume traverses in the process of performing x-ray spectroscopy on the sample within the microvolume.

19. A method according to claim [18] *1*, wherein the one or more dividers are formed of an impermeable material.

20. A method according to claim [18] *19*, wherein the impermeable material is an impermeable liquid.

21. A method according to claim [18] *19*, wherein the impermeable material is an impermeable solid.

22. A method according to claim [18] *1*, wherein the one or more dividers are formed of a permeable material.

23. A method according to claim [18] *1*, wherein the one or more dividers are formed of a semipermeable material.

27. A method according to claim [18] *1*, wherein at least one of the one or more dividers form an interface selected from the group consisting of liquid/liquid, liquid/gas interface, liquid/solid and liquid/sol-gel interface.

28. A method according to claim [18] *1*, wherein the one or more dividers are selected from the group consisting of a membrane, gel, frit, and matrix.

29. A method according to claim [18] *1*, wherein the one or more dividers function to modulate diffusion characteristics between adjacent crystallization samples.

30. A method according to claim [18] *1*, wherein at least one of the one or more dividers is formed of a semipermeable material which allows diffusion between adjacent crystallization samples.

33. A method [according to claim 11,] *for determining crystallization conditions for a protein, the method comprising:*
    *within a microfluidic device, delivering material to an enclosed microvolume via one or more lumens that each have a cross sectional diameter of less than 500 microns to form a plurality of different crystallization samples within the enclosed microvolume wherein the plurality of different crystallization samples are separated from each other within the enclosed microvolume by one or more dividers positioned within the enclosed microvolume, the plurality of different crystallization samples comprising a protein to be crystallized and crystallization conditions which vary among the plurality of different crystallization samples;*
    *allowing crystals of the protein to form in the plurality of crystallization samples within the microfluidic device;*
    *identifying which of the plurality of crystallization samples within the microfluidic device comprise a precipitate or a crystal of the protein; and*
    *performing x-ray spectroscopy on a precipitate or crystal within the microvolume*
    wherein x-ray spectroscopy is performed such that a portion of the crystal or precipitate that the x-ray beam traverses contains at least as many electrons as is otherwise traversed by the x-ray beam when traversing a device comprising the microvolume.

34. A method according to claim [11] *33*, wherein x-ray spectroscopy is performed such that a portion of the crystal or precipitate that the x-ray beam traverses contains at least three times as many electrons as is otherwise traversed by the x-ray beam when traversing a device comprising the microvolume.

35. A method according to claim [11] *33*, wherein x-ray spectroscopy is perfomed such that a portion of the crystal or precipitate that the x-ray beam traverses contains at least five times as many electrons as is otherwise traversed by the x-ray beam when traversing a device comprising the microvolume.

36. A method according to claim [11] *33*, wherein x-ray spectroscopy is perfomed such that a portion of the crystal or precipitate that the x-ray beam traverses contains at least ten times as many electrons as is otherwise traversed by the x-ray beam when traversing a device comprising the microvolume.

38. A method according to claim [11] *33*, wherein x-ray spectroscopy is perfomed such that a portion of the microvolume that the x-ray beam traverses contains at least half as many electrons as is contained in a material defining the portion of the microvolume that the x-ray beam traverses.

\* \* \* \* \*